United States Patent [19]

Bru-Magniez et al.

[11] Patent Number: 5,480,983
[45] Date of Patent: * Jan. 2, 1996

[54] ADENOSINE DERIVATIVES, PREPARATION METHODS AND PHARMACEUTICAL COMPOSITIONS CONTAINING THEM

[75] Inventors: Nicole Bru-Magniez, Paris; Timur Güngor, Rueil Malmaison; Jean-Marie Teulon, La Celle St. Cloud, all of France

[73] Assignee: Laboratoires UPSA, Agen, France

[*] Notice: The portion of the term of this patent subsequent to Apr. 5, 2011, has been disclaimed.

[21] Appl. No.: 256,081

[22] PCT Filed: Dec. 29, 1992

[86] PCT No.: PCT/FR92/01241

§ 371 Date: Jun. 29, 1994

§ 102(e) Date: Jun. 29, 1994

[87] PCT Pub. No.: WO93/14102

PCT Pub. Date: Jul. 22, 1993

Related U.S. Application Data

[63] Continuation-in-part of Ser. No. 832,576, Feb. 7, 1992, Pat. No. 5,229,505.

[30] Foreign Application Priority Data

Jan. 8, 1992 [FR] France ................................. 92 00138

[51] Int. Cl.⁶ .................................................. C07H 19/167

[52] U.S. Cl. .................................... 536/27.62; 536/27.22
[58] Field of Search .............................. 536/27.62, 27.72

[56] References Cited

U.S. PATENT DOCUMENTS 5,229,505  7/1993  Bru-Magniez et al. ............. 536/27.62

*Primary Examiner*—Nathan M. Nutter
*Attorney, Agent, or Firm*—Dennison, Meserole, Pollack & Scheiner

[57] ABSTRACT

The present invention relates to the derivatives of the formula

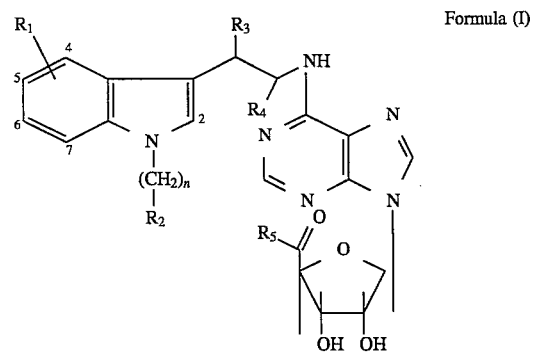

and their addition salts, and to their use in therapeutics, especially as analgesics and as antihypertensives.

15 Claims, No Drawings

ADENOSINE DERIVATIVES, PREPARATION METHODS AND PHARMACEUTICAL COMPOSITIONS CONTAINING THEM

This application is a continuation-in-part of U.S. application Ser. No. 07/832,576, filed Feb. 7, 1992, now U.S. Pat. No. 5,229,505.

The present invention relates, by way of novel products, to the adenosine derivatives of general formula (I) below and, if appropriate, their addition salts, in particular the pharmaceutically acceptable addition salts.

The compounds in question have a very valuable pharmacological profile insofar as they possess on the one hand, and in particular, analgesic properties, and on the other hand antihypertensive properties.

The present invention further relates to the method of preparing said products, to the synthesis intermediates and to the application of these products in therapeutics.

These adenosine derivatives have general formula (I):

Formula (I)

in which:

$R_1$ is a hydrogen atom, a halogen atom, a lower alkyl radical, a lower O-alkyl radical, a lower S-alkyl radical or a phenyl radical and can be located in the 2-, 4-, 5-, 6- or 7-position of the indole;

n is an integer from 0 to 4;

$R_2$ is a lower alkyl radical, a lower alkenyl radical, a lower alkynyl radical, a $C_3$–$C_7$-cycloalkyl radical or a lower O-alkyl radical;

a phenyl or naphthyl radical which is unsubstituted or substituted by one to four identical or different substituents selected from a halogen atom, a nitro, lower alkyl, lower O-alkyl or lower S-alkyl group and a group —$NR_7R_8$, $R_7$ and $R_8$ being the hydrogen atom or a lower alkyl radical;

a heterocyclic radical selected from pyridine and thiophene which is unsubstituted or substituted by one to four identical or different substituents selected from a halogen atom and a nitro, lower alkyl, lower O-alkyl or lower S-alkyl group;

or else, when n is equal to 2, 3 or 4, a group —$NR_9R_{10}$, $R_9$ and $R_{10}$ simultaneously being a lower alkyl radical or forming, together with the nitrogen atom to which they are attached, a heterocycle selected from morpholine, piperidine and pyrrolidine;

$R_3$ and $R_4$, which are identical or different, are the hydrogen atom or a lower alkyl radical; and $R_5$ is a group —$NHR_{11}$, $R_{11}$ being a lower alkyl radical, a $C_3$–$C_7$-cycloalkyl radical, a lower alkyl chain possessing an alcohol or ether functional group, or else a group —$(CH_2)_n$—$NR_9R_{10}$, n, $R_9$ and $R_{10}$ being as defined above.

Advantageously, the derivatives according to the invention are the derivatives of formula (I) given above in which:

$R_1$ is a hydrogen atom, a halogen atom, a lower alkyl radical, a lower O-alkyl radical, a lower S-alkyl radical or a phenyl radical and can be located in the 2- or 5-position of the indole;

n is an integer equal to 0, 1 or 2;

$R_2$ is a lower alkyl radical, a lower alkenyl radical, a lower alkynyl radical, a $C_3$–$C_7$-cycloalkyl radical or a lower O-alkyl radical;

a phenyl or naphthyl radical which is unsubstituted or substituted by one or two identical or different substituents selected from a halogen atom, a nitro, lower alkyl or lower O-alkyl group and a group —$NR_7R_8$, $R_7$ and $R_8$ being the hydrogen atom or a lower alkyl radical; 3 a heterocyclic radical selected from pyridine and thiophene which is unsubstituted or substituted by a halogen atom;

or else, when n=2, a group —$NR_9R_{10}$, $R_9$ and $R_{10}$ simultaneously being a lower alkyl radical or forming, together with the nitrogen atom to which they are attached, a heterocycle selected from morpholine, piperidine and pyrrolidine;

$R_3$ and $R_4$, which are identical or different, are the hydrogen atom or a lower alkyl radical; and $R_5$ is a group —$NHR_{11}$, $R_{11}$ being a lower alkyl radical, a $C_3$–$C_7$-cycloalkyl radical or a lower alkyl chain possessing an alcohol or ether functional group.

In the description and the claims, lower alkyl radical is understood as meaning a linear or branched hydrocarbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

In the description and the claims, lower alkenyl radical is understood as meaning a linear or branched hydrocarbon chain having from 1 to 6 carbon atoms and possessing a double bond, such as, for example, an ethenyl group, and lower alkynyl radical is understood as meaning a linear or branched hydrocarbon chain having from 1 to 6 carbon atoms and possessing a triple bond, such as, for example, an ethynyl group.

$C_3$–$C_7$-Cycloalkyl radical is understood as meaning a saturated cyclic radical, preferably a cyclopropyl, cyclobutyl, cyclopentyl, cyclohexyl or cycloheptyl radical.

Halogen is understood as meaning a chlorine, bromine, iodine or fluorine atom.

Lower alkyl chain possessing an alcohol functional group is understood as meaning a lower alkyl chain in which one of the hydrogen atoms has been substituted by a hydroxyl group. Such a chain is for example the 1-hydroxy-2-methylpropan-2-yl chain.

Lower alkyl chain possessing an ether functional group is understood as meaning a lower alkyl chain in which one of the hydrogen atoms has been substituted by a lower O-alkyl group. Such a chain is for example the 2-methoxyethyl chain.

Given the therapeutic potential of adenosine itself, numerous derivatives of this nucleoside have been described in the literature. The following documents may be cited as examples:

Journal of Medicinal Chemistry 1973, vol. 16, no. 4, pages 358–64

FR 2 154 527

EP 0 267 878
WO 88/03 148
WO 88/03 147
WO 86/00 310
WO 92/05 177
Biochemical Pharmacology 1974, vol. 23, pages 2283-89
U.S. Pat. No. 4,167,565
EP 0 232 813
U.S. Pat. No. 5,023,244

Among these numerous documents, essentially only two derivatives with the indole in the 6-position of the adenosine have been cited.

Thus: the article published in Journal of Medicinal Chemistry and the patent FR 2 154 527 both describe the same product: N-6-[2-(indol-3-yl)ethyl]adenosine (derivative A):

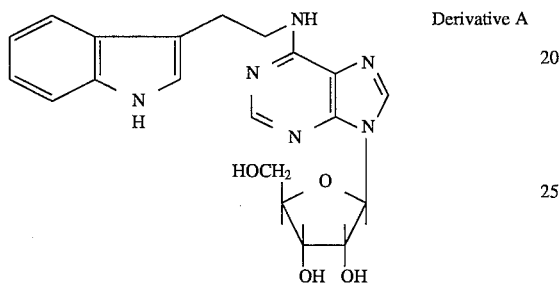

the article in Biochemical Pharmacology describes a 5-methoxytryptamine derivative, which is also cited in the document FR 2 154 527 (derivative B):

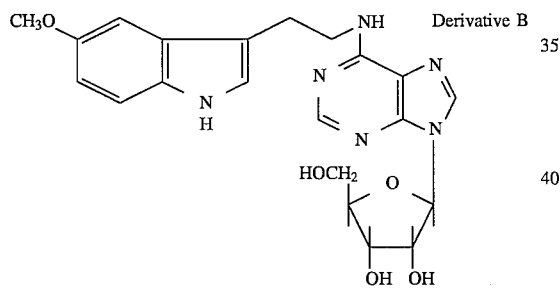

It may be noted that the article in Journal of Medicinal Chemistry describes derivative A as having a platelet aggregation inhibiting activity, whereas the French patent mentions effects on the central nervous system, the circulation and the heart, without being more precise. Biochemical Pharmacology specifies that derivative B has an antilipolytic activity.

It may be noted that, in the compounds described, on the one hand the indole derivatives are never substituted on the nitrogen atom of the indole, and on the other hand the sugar of the adenosine is intact.

Now, the Applicant has discovered that, surprisingly and unexpectedly, substitution of the nitrogen atom of the indole ring, combined with conversion of the primary alcohol of the sugar to an amide functional group, gives the products a particularly valuable pharmacological profile, especially in the field of analgesics.

In one variant, $R_1$ is the hydrogen atom.
In another variant, $R_1$ is a methyl radical.
In another variant, $R_1$ is a methoxy radical.
In one variant, n is a number equal to 0.
In another variant, n is a number equal to 1.
In another variant, n is a number equal to 2.

In one variant, $R_2$ is a methoxy radical.
In another variant, $R_2$ is a cyclopentane radical.
In another variant, $R_2$ is an isopropyl radical.
In another variant, $R_2$ is a 2,5-dimethylphenyl radical.
In another variant, $R_2$ is a piperidine radical.
In one variant, $R_3$ is the hydrogen atom.
In one variant, $R_4$ is the hydrogen atom.
In another variant, $R_4$ is a methyl radical.
In one variant, $R_5$ is an N-cyclopropylamine radical.

The particularly preferred compounds of the invention are selected from the derivatives of the formulae

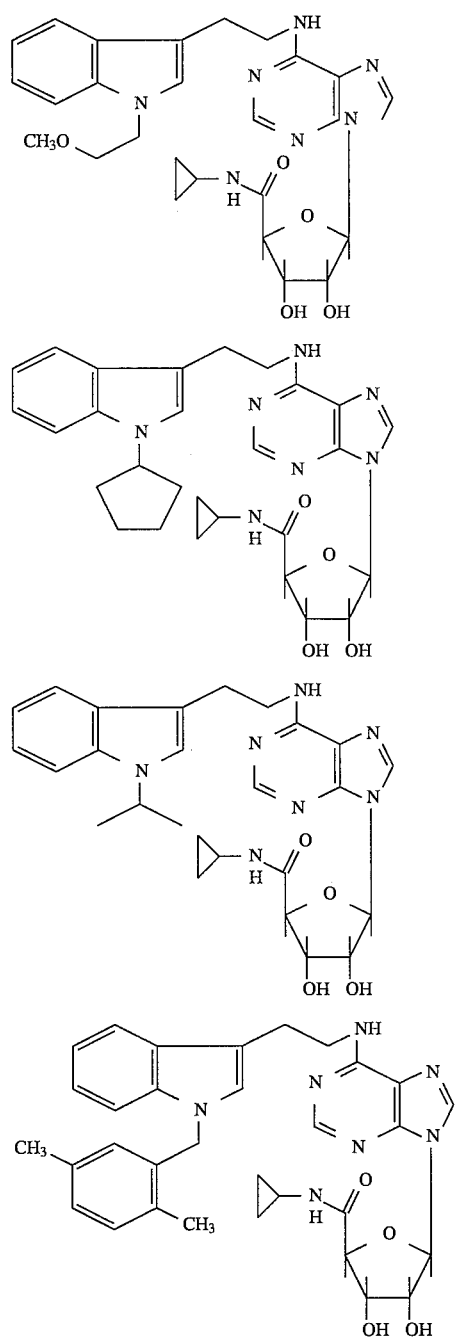

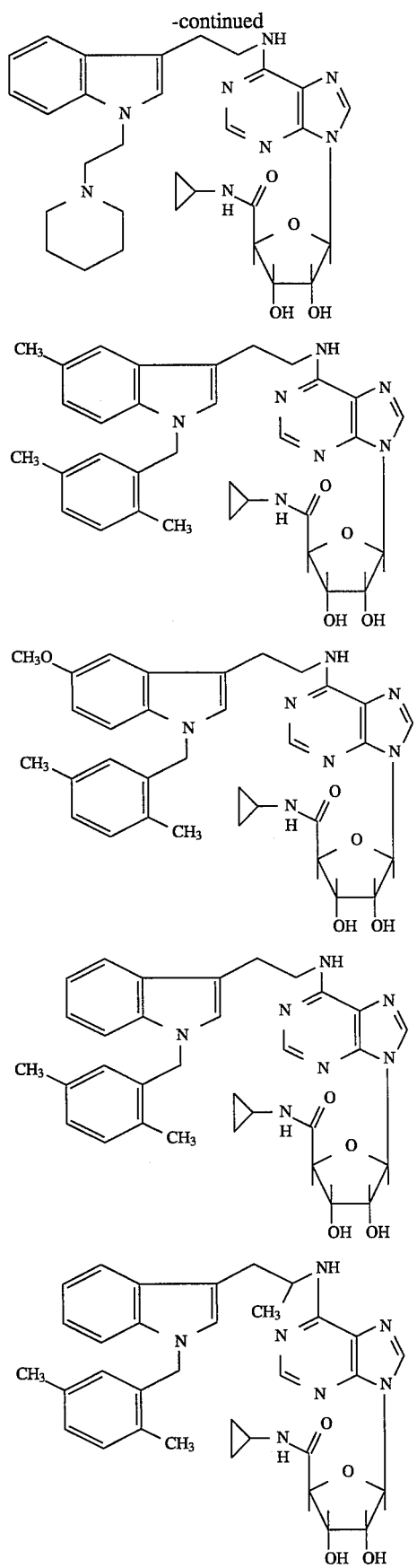

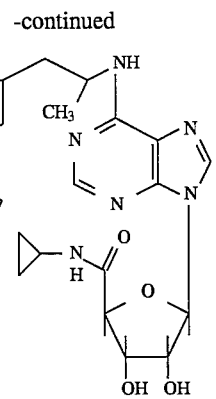

According to the invention, the compounds of formula (I) may be synthesized in the following manner:

Reaction of an amine of formula (II):

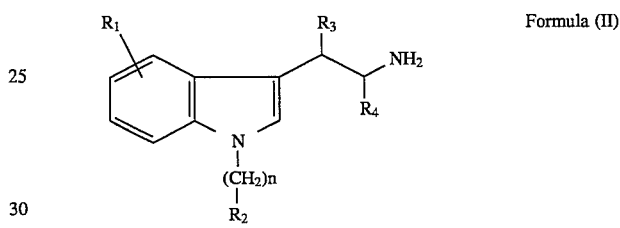

in which $R_1$, $R_2$, $R_3$, $R_4$ and n are as defined above, with the 6-halogenopurine ribosides of formula (III):

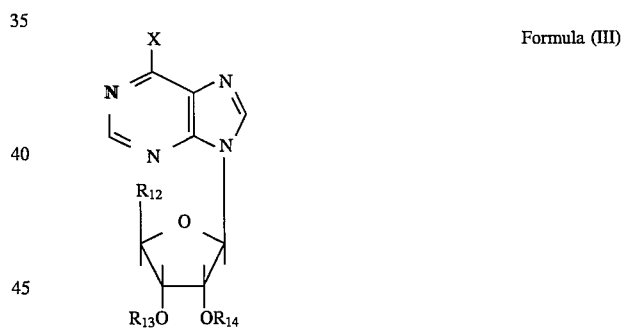

in which X is a halogen atom, preferably chlorine or bromine, $R_{12}$ is the group $COR_5$, $R_5$ being as defined above, or the $CH_2OH$ group, and $R_{13}$ and $R_{14}$ are protecting groups for the alcohol functional group, such as, for example, an acetyl, a benzoyl or a benzyl, or can together form another protecting group, for example of the dioxolan structure, in a solvent such as, for example, an alcohol or an aprotic solvent such as dimethylformamide, in the presence of a base such as triethylamine, pyridine or sodium, potassium or calcium carbonate, or else in the presence of two equivalents of the amine of formula (II), at a temperature of between 20° and 140° C., will give the compounds of formula (IV):

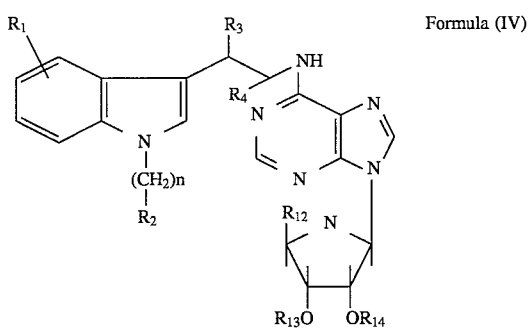

in which $R_1$, $R_2$, $R_3$, $R_4$, $R_{12}$, $R_{13}$, $R_{14}$ and n are as defined above.

If the indolamine derivative of formula (II) has a center of asymmetry, the compounds have to be considered either in the racemic form or in the optically active form. If it is desired to obtain the optically active derivative, care will be taken to separate the stereoisomers at the indolamine stage, prior to coupling with the 6-halogenopurine ribosides of formula (III), by conventional methods of optical isomer separation which are known to those skilled in the art, for example by recrystallization of the salts formed with an optically active tartaric acid. After separation of the optically active tartrates, the optically active base freed from its tartaric acid will be coupled with the 6-halogenopurine ribosides of formula (III).

In the case where the radical $R_{12}$ is the $CH_2OH$ group, it may be oxidized with chromium trioxide by the method described by:

R. R. SCHMIDT and H. J. FRITZ, Chem. Ber. 1970, 103, 1867, or with potassium permanganate in the presence of aqueous ammonia by the method described by:

P. J. HARPER and A. HAMPTON, J. Org. Chem. 1970, 35, no. 5, 1688, the resulting ribouronic acid then being converted to the acid chloride by reaction with thionyl chloride, for example, and then to an amide by reaction with an amine by the methods known to those skilled in the art. Deprotection of the secondary alcohols $OR_{13}$ and $OR_{14}$ may be carried out by different methods, for example in a basic medium such as ammoniacal alcohol, or in an acid medium such as a normal hydrochloric acid solution or a formic acid solution, at temperatures varying from 0° to 70° C. depending on the nature of the protecting groups.

These reaction sequences make it possible to convert the derivatives of formula (IV) to derivatives of formula (I).

The compounds of formula (II) may be obtained:

either by the direct alkylation of indolethylamine derivatives of formula (V):

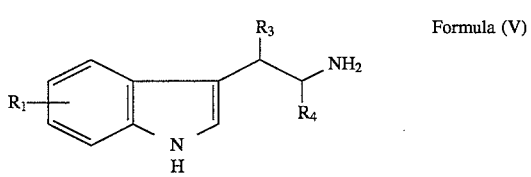

in which $R_1$, $R_3$ and $R_4$ are as defined above, which are commercially available or whose synthesis is described in the following literature:

P. L. JULIAN, E. W. MEYER and H. C. PRINTY, Heterocyclic Compounds, John Wiley and Sons, Inc. New York, 1952, vol. 3, chapter 1, p. 51–57, and J. HARLEY-MASON and A. H. JACKSON, J. Chem. Soc. 1954, 1165, with derivatives of formula (VI):

in which $R_2$ and n are as defined above, Y being a halogen atom, preferably chlorine or bromine, in the presence of a metalating agent such as sodium or lithium hydride, or of a sodium or potassium alcoholate, in an organic solvent such as an alcohol or such as dimethylformamide or N-methylpyrrolidone, at temperatures of between 0° and 60° C.;

or by the alkylation of a 3-formylindole of formula (VII):

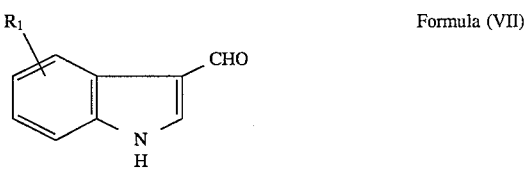

in which $R_1$ is as defined above, with above-mentioned derivatives of formula (VI), in the presence of a metalating agent such as sodium or lithium hydride, or of a sodium or potassium alcoholate or sodium or potassium carbonate, in an organic solvent such as an alcohol or dimethylformamide, to give the derivatives of formula (VIII):

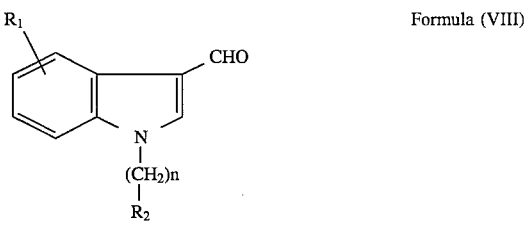

in which $R_1$, $R_2$ and n are as defined above.

These derivatives are then reacted with the appropriate nitroalkane, in the presence of ammonium acetate, to give the nitrovinylindoles of formula (IX):

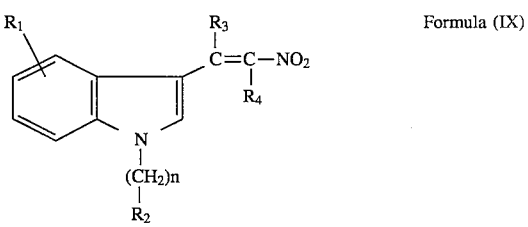

in which $R_1$, $R_2$, $R_3$, $R_4$ and n are as defined above.

These derivatives are then reduced by catalytic hydrogenation in the presence of Raney nickel, or with lithium aluminum hydride, to give the compounds of formula (II).

Other methods of synthesizing indolethylamine derivatives are generally described in the literature and can be used. An example which may be mentioned is the method of synthesis which consists in reacting oxalyl chloride with the appropriate indole according to the following reference:

M. E. SPEETER and W. C. ANTHONY, J. Am. Chem. Soc. 1954, 76, 6208, and then amidating the product and reducing the amide functional group with lithium aluminum hydride.

The 3-formylindoles of formula (VII) used in these syntheses are commercially available or are known to those skilled in the art, for example from the following reference:

Organic Syntheses Coll. vol. IV, 539, or can be obtained by methods described in the literature, for example in:

Organic Syntheses Coll. vol. IV, 542.

The 6-halogenopurines of formula (III) are prepared from inosine by methods described in the following literature:

R. R. SCHMIDT and H. J. FRITZ, Chem. Ber. 1970, 103, 1867,

H. M. KISSMAN and M. J. WEISS, J. Org. Chem. 1956, 21, 1053,

B. R. BAKER, K. HEWSON, H. J. THOMAS and J. A. JOHNSON JR, J. Org. Chem. 1957, 22, 954, and J. ZEMLICKA and F. SORM, Coll. Czech. Chem. Commun. 1965, 30, (6), 1880.

The compounds of formula (I) as defined above, and their addition salts, in particular the pharmaceutically acceptable addition salts, possess a good affinity for adenosine receptors. This affinity gives them a good analgesic activity but also antihypertensive properties.

These properties justify the application of the derivatives of formula (I) in therapeutics and the invention further relates, by way of drugs, to the products as defined by formula (I) above, and their addition salts, in particular the pharmaceutically acceptable addition salts.

Thus the invention also covers a pharmaceutical composition which comprises a pharmaceutically effective amount of at least one compound of formula (I) as defined above, or one of its pharmaceutically acceptable addition salts, which may or may not be incorporated in a pharmaceutically acceptable excipient, vehicle or carrier.

These compositions can be administered by the buccal, rectal, parenteral, transdermal or ocular route.

These compositions can be solid or liquid and can be in the pharmaceutical forms commonly used in human medicine, such as, for example, simple or coated tablets, gelatin capsules, granules, suppositories, injectable preparations, transdermal systems and eye lotions. They are prepared by the customary methods. The active principle, which consists of a pharmaceutically effective amount of at least one compound of formula (I) as defined above, or one of its pharmaceutically acceptable addition salts, can be incorporated therein with excipients normally employed in these pharmaceutical compositions, such as talc, gum arabic, lactose, starch, magnesium stearate, polyvidone, cellulose derivatives, cacao butter, semisynthetic glycerides, aqueous or non-aqueous vehicles, fatty substances of animal or vegetable origin, glycols, various wetting agents, dispersants or emulsifiers, silicone gels, certain polymers or copolymers, preservatives, flavorings and colors.

The invention also covers a pharmaceutical composition with analgesic activity affording especially a favorable treatment for pain, which comprises a pharmaceutically effective amount of at least one compound of formula (I) given above, or one of its pharmaceutically acceptable addition salts, which may or may not be incorporated in a pharmaceutically acceptable excipient, vehicle or carrier.

The invention also covers a pharmaceutical composition with antihypertensive activity affording a favorable treatment for hypertension, which comprises a pharmaceutically effective amount of at least one compound of formula (I) given above, or one of its pharmaceutically acceptable addition salts, which may or may not be incorporated in a pharmaceutically acceptable excipient, vehicle or carrier.

The invention also covers a method of preparing a pharmaceutical composition, which comprises incorporating a pharmaceutically effective amount of at least one compound of formula (I) as defined above, or one of its pharmaceutically acceptable addition salts, into a pharmaceutically acceptable excipient, vehicle or carrier. In one embodiment, a pharmaceutical composition with analgesic activity is prepared which affords especially a favorable treatment for pain; in another embodiment, a pharmaceutical composition with antihypertensive activity is prepared which affords especially a favorable treatment for hypertension.

In another variant, a pharmaceutical composition is formulated as gelatin capsules or tablets containing from 5 to 300 mg of active ingredient, or as injectable preparations containing from 0.1 mg to 100 mg of active ingredient. Formulations as suppositories, ointments, creams, gels or aerosol preparations may also be used.

The invention also covers a method of therapeutic treatment for mammals, which comprises administering to this mammal a therapeutically effective amount of at least one compound of formula (I) as defined above, or one of its pharmaceutically acceptable addition salts. In one variant of this method of treatment, the compound of formula (I), either by itself or in association with a pharmaceutically acceptable excipient, is formulated as gelatin capsules or tablets containing from 5 mg to 300 mg of active ingredient for oral administration, or as injectable preparations containing from 0.1 to 100 mg of active ingredient, or else as suppositories, ointments, creams, gels or aerosol preparations.

In human and animal therapeutics, the compounds of formula (I) and their salts can be administered by themselves or in association with a physiologically acceptable excipient, in any form, in particular in the form of gelatin capsules or tablets for oral administration or in the form of an injectable solution for parenteral administration. Other forms of administration, such as suppositories, ointments, creams, gels or aerosol preparations, can be envisaged.

As will be clearly apparent from the pharmacological tests given at the end of the description, the compounds according to the invention can be administered in human therapeutics for the above-mentioned indications, orally in the form of tablets or gelatin capsules containing from 5 mg to 300 mg of active ingredient, or parenterally in the form of injectable preparations containing from 0.1 mg to 100 mg of active ingredient, in one or more daily administrations for an adult with an average weight of 60 to 70 kg.

In animal therapeutics, the daily dose which can be used should normally be between 0.1 and 50 mg per kg by oral administration and between 0.01 and 1 mg per kg by intravenous administration.

Further characteristics and advantages of the invention will be understood more clearly from the following description of some Examples, which in no way imply a limitation but are given by way of illustration.

EXAMPLE 1

β-D-Ribofuranuronamido-1-(6-chloro-9H-purin-9-yl)-
N-cyclopropyl-1-deoxy-2,3-O-(1-methylethylidene)

Formula (III): X=Cl, $R_{12}$:

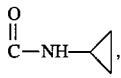

$R_{13}$, $R_{14}$: isopropylidene 20 g of 2',3'-O-isopropylidene-6-chloropurine-5'-uronic acid, prepared according to SCHMIDT R. R. and FRITZ H. J., Chem. Ber. 1970, 103(6), 1867–71, in 500 ml of anhydrous CHCl stabilized with amylene, are refluxed for 5 h in the presence of 86 ml of $SOCl_2$ and 10 ml of anhydrous DMF.

The excess $SOCl_2$ and the solvents are distilled. The residue is taken up with 200 ml of anhydrous chloroform and added dropwise, under nitrogen, to a mixture of 150 ml of $CHCl_3$ and 41 ml of cyclopropylamine, cooled to 5° C. beforehand. The temperature of the reaction mixture is kept below 10° C. during the addition of the acid chloride.

The mixture is left to react for a further 30 min and then washed 3 times with a dilute HCl solution and then with a sodium bicarbonate solution. A final washing with water, followed by drying and evaporation of the solvent, gives 26.3 g of a brown oil.

Purification by chromatography on silica gel (eluent: $CH_2Cl_2$ 90%/acetone 10%) gives 15.7 g of β-D-ribofuranuronamido-1-(6-chloro-9H-Purin-9-yl)-N-cyclopropyl-1-deoxy-2,3-O-(1-methylethylidene) in the form of an amorphous solid.

The compounds of Examples 2 to 4 were prepared by the procedure of Example 1 using the appropriate amines:

EXAMPLE 2

β-D-Ribofuranuronamido-1-(6-chloro-9H-Purin-9-yl)-
1-deoxy-N-ethyl-2,3-O-(1-methylethylidene)

Formula (III): X=Cl, $R_{12}$:

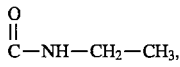

$R_{13}$, $R_{14}$: isopropylidene

A yellowish oil purified by chromatography on silica gel (eluent: chloroform 95%/methanol 5%) to give a solid melting at 91° C.

EXAMPLE 3

β-D-Ribofuranuronamido-1-(6-chloro-9H-purin-9-yl)-
1-deoxy-N-(1-hydroxy-2-methylpropan-2-yl)-2,3-
O-(1-methylethylidene)

Formula (III): X=Cl, $R_{12}$:

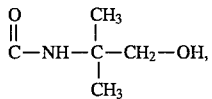

A brown oil purified by chromatography on silica gel (eluent: chloroform 90%/methanol 10%).

EXAMPLE 4

β-D-Ribofuranuronamido-1-(6-chloro-9H-purin-9-yl)-
1-deoxy-N-isopropyl-2,3-O-(1-methylethylidene)

Formula (III): X=Cl, $R_{12}$:

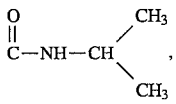

$R_{13}$,$R_4$: isopropylidene

An orange oil purified by chromatography on silica gel (eluent: $CHCl_3$ 90%/acetone 10%).

EXAMPLE 5

1-(4-Chlorobenzyl)-3-formylindole

Formula (VIII): $R_1$=H, n=1, $R_2$=4-chlorophenyl

A solution of 58 g of 3-formylindole, 55.9 g of $K_2CO_3$ and 70.9 g of p-chlorobenzyl chloride in 200 ml of DMF is refluxed for 2 h. After cooling, the mixture is poured into 2 l of water and triturated. The precipitate obtained is filtered off, washed with water and then taken up with isopropanol, filtered off, compressed and washed with pentane to give 120 g of a cream-colored solid.

Purification by recrystallization from ethanol gives 84.4 g of 1-(4-chlorobenzyl)-3-formylindole melting at 122° C.

The following compounds of Examples 6 to 16 were prepared by the method of Example 5:

EXAMPLE 6

1-Benzyl-3-formylindole

Formula (VIII): $R_1$=H, n=1, $R_2$=phenyl

Recrystallization from ethanol. Melting point: 111° C. (literature: 113°–114° C.— A. KALIR and S. SZARA, J. Med. Chem. (1966), vol. 9, p. 793).

EXAMPLE 7

1-(2,6-Dichlorobenzyl)-3-formylindole

Formula (VIII): $R_1$=H, n=1, $R_2$=2,6-dichlorophenyl

Recrystallization from 2-methoxyethanol. Melting point: 160° C.

EXAMPLE 8

1-(Naphth-1-ylmethyl)-3-formylindole

Formula (VIII): $R_1$=H, n=1, $R_2$=naphthyl

A crude solid used as such in the next step.

EXAMPLE 9

3-Formyl-1-(pyrid-3-yl)indole

Formula (VIII): $R_1$=H, n=1, $R_2$=pyrid-3-yl

Purification by chromatography on silica gel (eluent: $CHCl_3$ 95%/methanol 5%). Melting point: 88° C.

EXAMPLE 10

1-(4-Methylbenzyl)-3-formylindole

Formula (VIII): $R_1$=H, n=1, $R_2$=4-methylphenyl

A crude solid used as such in the next step. Melting point: 118° C.

EXAMPLE 11

1-(3,4-Dimethylbenzyl)-3-formylindole

Formula (VIII): $R_1$=H, n=1, $R_2$=3,4-dimethylphenyl

A brown oil used as such in the next step.

EXAMPLE 12

1-(2,5-Dimethylbenzyl)-3-formylindole

Formula (VIII): $R_1$=H, n=1, $R_2$=2,5-dimethylphenyl

A crude solid used as such in the next step. Melting point: 139° C.

EXAMPLE 13

1-(2-Methoxyethyl)-3-formylindole

Formula (VIII): $R_1$=H, n=2, $R_2$=methoxy

A brown oil used as such in the next step.

EXAMPLE 14

1-Cyclopentyl-3-formylindole

Formula (VIII): $R_1$=H, n=0, $R_2$=cyclopentyl

A brown oil purified by chromatography on silica gel (eluent: chloroform 90%/methanol 10%).

EXAMPLE 15

3-Formyl-1-isopropylindole

Formula (VIII): $R_1$=H, n=0, $R_2$=isopropyl

A brown oil used as such in the next step.

EXAMPLE 16

3-Formyl-1-(2-N-morpholinoethyl)indole

Formula (VIII): $R_1$=H, n=2, $R_2$=N-morpholino

A solid used as such in the next step. Melting point: 80° C.

EXAMPLE 17

1-(4-Chlorobenzyl)-3-(2-nitrovinyl)indole

Formula (IX): $R_1$=H, n=1, $R_2$=4-chlorophenyl, $R_3$=$R_4$=H 80.9 g of 1-(4-chlorobenzyl)-3-formylindole, prepared in Example 5, 18 g of ammonium acetate and 300 ml of nitromethane are refluxed for 30 min.

An orange precipitate appears after cooling. It is filtered off and washed with water and then with isopropanol and hexane to give 81.1 g of orange crystals of 1-(4-chlorobenzyl)-3-(2-nitrovinyl)indole. Melting point: 178° C.

The nitrovinylindoles of Examples 18 to 28 were prepared by the procedure of Example 17:

EXAMPLE 18

1-Benzyl-3-(2-nitrovinyl)indole

Formula (IX): $R_1$=H, n=1, $R_2$=phenyl, $R_3$=$R_4$=H

Melting point: 130° C.

EXAMPLE 19

1-(2,6-Dichlorobenzyl)-3-(2-nitrovinyl)indole

Formula (IX): $R_1$=H, n=1, $R_2$=2,6-dichlorophenyl, $R_3$=$R_4$=H

Melting point: 170° C.

EXAMPLE 20

1-Naphthylmethyl-3-(2-nitrovinyl)indole

Formula (IX): $R_1$=H, n=1, $R_2$=naphthyl, $R_3$=$R_4$=H

Melting point: 196° C.

EXAMPLE 21

1-(Pyrid-3-ylmethyl)-3-(2-nitrovinyl)indole

Formula (IX): $R_1$=H, n=1, $R_2$=pyrid-3-yl, $R_3$=$R_4$=H

Melting point: 165°–170° C.

EXAMPLE 22

1-(4-Methylbenzyl)-3-(2-nitrovinyl)indole

Formula (IX): $R_1$=H, n=1, $R_2$=4-methylphenyl, $R_3$=$R_4$=H

An orange oil purified by chromatography on silica gel (eluent: chloroform 95%/isopropylamine 5%).

EXAMPLE 23

1-(3,4-Dimethylbenzyl)-3-(2-nitrovinyl)indole

Formula (IX): $R_1$=H, n=1, $R_2$=3,4-dimethylphenyl, $R_3$=$R_4$=H

Melting point: 135° C.

EXAMPLE 24

1-(2,5-Dimethylbenzyl)-3-nitrovinylindole

Formula (IX): $R_1$=H, n=1, $R_2$=2,5-dimethylphenyl, $R_3$=$R_4$=H

Melting point: 145° C.

EXAMPLE 25

1-(2-Methoxyethyl)-3-(2-nitrovinyl)indole

Formula (IX): $R_1$=H, n=2, $R_2$=methoxy, $R_3$=$R_4$=H

Melting point: 132° C.

EXAMPLE 26

1-Cyclopentyl-3-(2-nitrovinyl)indole

Formula (IX): $R_1$=H, n=0, $R_2$=cyclopentyl, $R_3$=$R_4$=H

An orange oil purified by chromatography on silica gel. Eluent: methylene chloride.

EXAMPLE 27

1-Isopropyl-3-(2-nitrovinyl)indole

Formula (IX): $R_1$=H, n=0, $R_2$=iso- propyl, $R_3$=$R_4$=H
An orange oil used as such in the next step.

EXAMPLE 28

1-(2-N-Morpholinoethyl)-3-(2-nitrovinyl)indole

Formula (IX): $R_1$=H, n=2, $R_2$=N-morpholino, $R_3$=$R_4$=H
Melting point: 114° C.

EXAMPLE 29

1-(4-Chlorobenzyl)-3-(2-aminoethyl)indole

Formula (II): $R_1$=H, n=1, $R_2$=4-chlorophenyl, $R_{=R4}$=H
52.5 g of $LiAlH_4$ are added in small portions to 500 ml of anhydrous THF. The temperature is left to rise to 50° C. Without cooling this solution, a solution of 78.2 g of 1-(4-chlorobenzyl)-3-(2-nitrovinyl)indole, prepared in Example 17, in 1000 ml of anhydrous THF is introduced dropwise.

The mixture is refluxed for 1 h 30 min and cooled. A saturated aqueous solution of $Na_2SO_4$ is introduced dropwise and the mixture is filtered on Célite 545. After decantation, the organic phase concentrated to give an orange oil.

The compound is purified firstly by distillation (boiling point: 180°–188° C. under 0.1 mm of mercury) and then by recrystallization of the hydrochloride from ethanol to give 38.1 g of 1-(4-chlorobenzyl)-3-(2-aminoethyl)indole hydrochloride. Melting point of the base: 87° C. Melting point of the hydrochloride: 212° C.

EXAMPLE 30

1-(4-Chlorobenzyl)-3-(2-aminoethyl)indole

Formula (II): $R_1$=H, n=1, $R_2$=4-chlorophenyl, $R_3$=$R_4$=H 10 g of 3-aminoethylindole are dissolved in 50 $cm^3$ of DMF. 5.6 g of NaH (60%) are then introduced.

The mixture is stirred for 30 min at room temperature.

A solution of 11.2 g of p-chlorobenzyl chloride in 10 ml of DMF is introduced dropwise. The mixture is heated at 55° C. for 2 h and cooled. The insoluble material is filtered off. The filtrate is concentrated under vacuum and the residue is taken up with methylene chloride and washed with water. After drying, the organic phase is concentrated to give 20.4 g of a brown oil.

Purification by chromatography on silica gel (eluent: $CHCl_3$ 95%/isopropylamine 5%) gives 9.7 g of 1 -(4-chlorobenzyl)-3-(2-aminoethyl)indole. Melting point of the hydrochloride: 214° C.

The following compounds of Examples 31 to 45 were prepared by one of the procedures of Examples 29 or 30:

EXAMPLE 31

1-Benzyl-3-(2-aminoethyl)indole

Formula (II): $R_1$=H, n=1, $R_2$=phenyl, $R_3$=$R_4$=H
The hydrochloride purified by recrystallization from isopropanol. Melting point: 176–178° C.

EXAMPLE 32

1-(2,6-Dichlorobenzyl)-3-(2-aminoethyl)indole

Formula (II): $R_1$=H, n=1, $R_2$=2,6-dichlorophenyl, $R_3$=$R_4$=H
Melting point: 68° C.

EXAMPLE 33

1-Naphthylmethyl-3-(2-aminoethyl)indole

Formula (II): $R_1$=H, n=1, $R_2$=naphthyl, $R_3$=$R_4$=H
An orange oil purified by chromatography on silica gel (eluent: chloroform 95%/isopropylamine 5%).

EXAMPLE 34

1-(Pyrid-3-ylmethyl)-3-(2-aminoethyl)indole

Formula (II): $R_1$=H, n=1, $R_2$=pyrid-3-yl, $R_3$=$R_4$=H
An oil purified by chromatography on silica gel (eluent: chloroform 95%/isopropylamine 5%).

EXAMPLE 35

1-(4-Methylbenzyl)-3-(2-aminoethyl)indole

Formula (II): $R_1$=H, n=1, $R_2$=4-methylphenyl, $R_3$=$R_4$=H
An orange oil purified by chromatography on silica gel (eluent: chloroform 95%/isopropylamine 5%).

EXAMPLE 36

1-(3,4-Dimethylbenzyl)-3-(2-aminoethyl)indole

Formula (II): $R_1$=H, n=1, $R_2$=3,4-dimethylphenyl, $R_3$=$R_4$=H
A colorless oil purified by chromatography on silica gel (eluent: methylene chloride 95%/isopropylamine 5%).

EXAMPLE 37

1-(2,5-Dimethylbenzyl)-3-(2-aminoethyl)indole

Formula (II): $R_1$=H, n=1, $R_2$=2,5-dimethylphenyl, $R_3$=$R_4$=H
An orange oil purified by chromatography on silica gel (eluent: methylene chloride 95%/isopropylamine 5%).

EXAMPLE 38

1-(2-Methoxyethyl)-3-(2-aminoethyl)indole

Formula (II): $R_1$=H, n=2, $R_2$=methoxy, $R_3$=$R_4$=H
An orange oil purified by chromatography on silica gel (eluent: chloroform 90%/isopropylamine 10%).

EXAMPLE 39

1-Cyclopentyl-3-(2-aminoethyl)indole

Formula (II): $R_1$=H, n=0, $R_2$=cyclopentyl, $R_3$=$R_4$=H
A yellowish oil purified by chromatography on silica gel (eluent: chloroform 95%/isopropylamine 5%).

17

EXAMPLE 40

1-Isopropyl-3-(2-aminoethyl)indole

Formula (II): $R_1$=H, n=0, $R_2$=isopropyl, $R_3$=$R_4$=H

An orange oil purified by chromatography on silica gel (eluent: chloroform 95%/isopropylamine 5%).

EXAMPLE 41

1-(2-N,N-Dimethylaminoethyl)-3-(2-aminoethyl)indole

Formula (II): $R_1$=H, n=2, $R_2$=N,N-dimethylamino, $R_3$=$R_4$=H

An orange oil purified by chromatography on silica gel (eluent: chloroform 95%/isopropylamine 5%).

EXAMPLE 42

1-(2-N-Morpholinoethyl)-3-(2-aminoethyl)indole

Formula (II): $R_1$=H, n=2, $R_2$=N-morpholino, $R_3$=$R_4$=H

An orange oil purified by chromatography on silica gel (eluent: chloroform 95%/isopropylamine 5%).

EXAMPLE 43

1-(2-N-Piperidinoethyl)-3-(2-aminoethyl)indole

Formula (II): $R_1$=H, n=2, $R_2$=N-piperidino, $R_3$=$R_4$=H

An orange oil purified by chromatography on silica gel (eluent: methylene chloride 95%/isopropylamine 5%).

EXAMPLE 44

1-(N-Pyrrolidinoethyl)-3-(2-aminoethyl)indole

Formula (II): $R_1$=H, n=2, $R_2$=N-pyrrolidino, $R_3$=$R_4$=H

An orange oil purified by chromatography on silica gel (eluent: methylene chloride 95%/isopropylamine 5%).

EXAMPLE 45

1-(3,4-Dichlorobenzyl)-3-(2-aminoethyl)indole

Formula (II): $R_1$=H, n=1, $R_2$ =3,4-dichlorophenyl, $R_3$=$R_4$=H

Melting point: 196° C.

EXAMPLE 46

β-D-Ribofuranuronamido-1-[6-[[2-[1-(4 -chlorobenzyl)indol-3-yl]ethyl]amino]-9 H-purin-9-yl]-N-cyclopropyl-1-deoxy-2,3-O-(1 -methylethylidene)

Formula (IV): $R_1$=H, n=1, $R_2$=4-chlorophenyl, $R_3$=$R_4$=H, $R_{12}$=

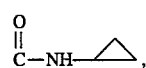

$R_{13}$, $R_{14}$=

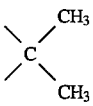

Under a stream of nitrogen, 49 g of 1-(4-chlorobenzyl)-3-(2-aminoethyl)indole hydrochloride, prepared by one of the procedures of Examples 29 or 30, are suspended in 100 ml of ethanol. The suspension is neutralized with 5.1 ml of triethylamine, after which 4.1 g of β-D-ribofuranuronamido-1-(6-chloro-9H-purin-9 -yl)-N-cyclopropyl-1-deoxy-2,3-O-(1-methylethylidene), prepared in Example 1, are added.

The whole is refluxed for 7 h and left to stand overnight. The solvent is evaporated off and the residue is taken up with chloroform, washed with water, dried and concentrated. The solid obtained is chromatographed on silica gel (eluent: chloroform 90%/methanol 10%) to give 7.2 g of an amorphous solid.

The derivatives of Examples 47 to 59 were prepared in the form of amorphous solids by the procedure of Example 46 using the uronamide of Example 1:

EXAMPLE 47

β-D-Ribofuranuronamido-N-cyclopropyl-1 -deoxy-1-[6-[[2-[1-(2-methoxyethyl)indol-3 -yl]ethyl]amino]-9H-purin-9-yl]-2,3-O-(1 -methylethylidene)

Formula (IV): $R_1$=H, n=2, $R_2$=methoxy, $R_3$=$R_4$=H, $R_{12}$=

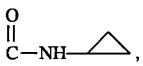

$R_{13}$,$R_{14}$=

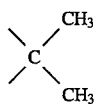

EXAMPLE 48

β-D-Ribofuranuronamido-1-[6-[[2-[1 -cyclopentylindol-3-yl]ethyl]amino]-9H-purin-9 -yl]-N-cyclopropyl-1-deoxy-2,3-O-(1 -methylethylidene)

Formula (IV): $R_1$=H, n=0, $R_2$=cyclopentyl, $R_3$=$R_4$=H, $R_{12}$=

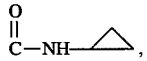

$R_{13}$, $R_{14}$=

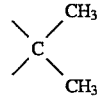

EXAMPLE 49

β-D-Ribofuranuronamido-N-cyclopropyl-1
-deoxy-1-[6-[[2-[1-isopropylindol-3-yl]
-ethyl]amino]-9H-purin-9-yl]-2,3-O-(1
-methylethylidene)

Formula (IV): $R_1$=H, n=0, $R_2$=isopropyl, $R_3$=$R_4$=H, $R_{12}$=

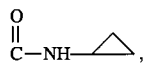

$R_{13}$,$R_{14}$=

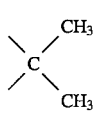

EXAMPLE 50

β-D-Ribofuranuronamido-N-cyclopropyl-1
-deoxy-1-[6-[[2-[1-(4-methylbenzyl)indol-3
-yl]ethyl]amino]-9H-purin-9-yl]-2,3-O-(1
-methylethylidene)

Formula (IV): $R_1$=H, n=1, $R_2$=4-methylphenyl, $R_3$=$R_4$=H, $R_{12}$=

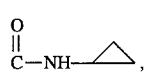

$R_{13}$,$R_{14}$=

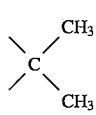

EXAMPLE 51

β-D-Ribofuranuronamido-N-cyclopropyl-1
-deoxy-1-[6-[[2-[1-(3,4
-dimethylbenzyl)indol-3-yl]ethyl]amino]-9H-purin-9-
yl]-2,3-O-(1-methylethylidene)

Formula (IV): $R_1$=H, n=1, $R_2$=3,4-dimethylphenyl, $R_3$=$R_4$=H, $R_{12}$=

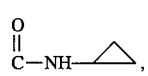

$R_{13}$,$R_{14}$=

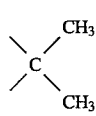

EXAMPLE 52

β-D-Ribofuranuronamido-N-cyclopropyl-1
-deoxy-1-[6-[[2-[1-(2,5
-dimethylbenzyl)indol-3-yl]ethyl]amino]-9H-
purin-9-yl]-2,3-O-(1-methylethylidene)

Formula (IV): $R_1$=H, n=1, $R_2$=2,5-dimethylphenyl, $R_3$=$R_4$=H, $R_{12}$=

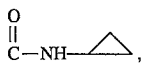

$R_{13}$,$R_{14}$=

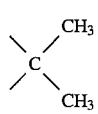

EXAMPLE 53

β-D-Ribofuranuronamido-N-cyclopropyl-1
-deoxy-1-[6-[[2-[1-(2
-N-morpholinoethyl)indol-3-yl]ethyl]amino]-9H-purin-9-yl]-2,3
-O-(1-methylethylidene)

Formula (IV): $R_1$=H, n=2, $R_2$=morpholino, $R_3$=$R_4$=H, $R_{12}$=

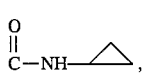

$R_{13}$,$R_{14}$=

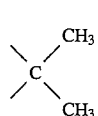

EXAMPLE 54

β-D-Ribofuranuronamido-N-cyclopropyl-1
-deoxy-1-[6-[[2-[1-(2
-N,N-dimethylaminoethyl)indol-3-yl]ethyl]amino]-
9H-purin-9-yl]-2,3-O-(1-methylethylidene)

Formula (IV): $R_1$=H, n=2, $R_2$=N,N-dimethylamino, $R_3$=$R_4$=H, $R_{12}$=

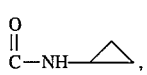

$R_{13}$,$R_{14}$=

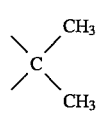

EXAMPLE 55

β-D-Ribofuranuronamido-N-cyclopropyl-1
-deoxy-2,3-O-(1-methylethylidene)-1-[6-[[2
-[1-(2-N-piperidinoethyl)indol-3-yl]ethyl1]
-amino]-9H-purin-9-yl]

Formula (IV): $R_1$=H, n=2, $R_2$=N-piperidino, $R_3$=$R_4$=H $R_{12}$=

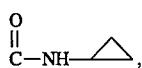

$R_{13}, R_{14}$=

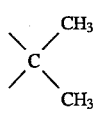

EXAMPLE 56

β-D-Ribofuranuronamido-N-cyclopropyl-1
-deoxy-2,3-O-(1-methylethylidene)-1-[6-[[2
-[1-(2-N-pyrrolidinoethyl)indol-3-yl]ethyl]
-amino]-9H-purin-9-yl]

Formula (IV): $R_1$=H, n=2, $R_2$= N-pyrrolidino, $R_3$=$R_4$=H, $R_{12}$=

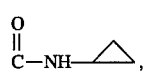

$R_{13}, R_{14}$=

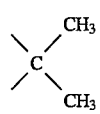

EXAMPLE 57

β-D-Ribofuranuronamido-N-cyclopropyl-1
-deoxy-1-[6-[[2-[1-(3,4
-dichlorobenzyl)indol-3-yl]ethyl]amino]-9H-purin-
9-yl]-2,3-O-(1-methylethylidene)

Formula (IV): $R_1$=H, n=1, $R_2$=3,4 -dichlorophenyl, $R_3$=$R_4$=H, $R_{12}$=

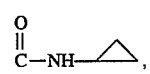

$R_{13}, R_{14}$=

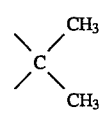

EXAMPLE 58

β-D-Ribofuranuronamido-N-cyclopropyl-1
-deoxy-2,3-O-(1-methylethylidene)-1-[6-[[2
-[1-(pyrid-3-ylmethyl)indol-3-yl]ethyl]
-amino]-9H-purin-9-yl]

Formula (IV): $R_1$=H, n=1, $R_2$=pyrid-3-yl, $R_3$=$R_4$=H, $R_{12}$=

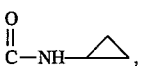

$R_{13}, R_{14}$=

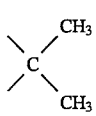

EXAMPLE 59

β-D-Ribofuranuronamido-N-cyclopropyl-1
-deoxy-2,3-O-(1-methylethylidene)-1-[6-[[2
-[1-(naphth-1-ylmethyl)indol-3-yl]ethyl]
-amino]-9H-purin-9-yl]

Formula (IV): $R_1$=H, n=1, $R_2$=naphth-1-yl, $R_3$=$R_4$=H, $R_{12}$=

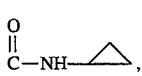

$R_{13}, R_{14}$=

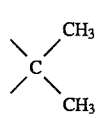

The compound of Example 60 was prepared by the procedure of Example 46 using the uronamide prepared in EXAMPLE 3:

EXAMPLE 60

β-D-Ribofuranuronamido-1-[6-[[2-[1-(4
-chlorobenzyl)indol-3-yl]ethyl]amino]-9
H-purin-9-yl]-1-deoxy-N-(1,1-dimethyl-2
-hydroxyethyl)-2,3-O-(1-methylethylidene)

Formula (IV): $R_1$=H, n=1, $R_2$=4 -chlorophenyl, $R_3$=$R_4$=H, $R_{12}$=

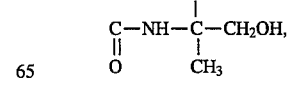

$R_{13}, R_{14}$=

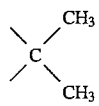

EXAMPLE 61

β-D-Ribofuranuronamido-1-[6-[[2-[1-(4
-chlorobenzyl)indol-3-yl]ethyl]amino]-9
H-purin-9-yl]-N-cyclopropyl-1-deoxy Formula (I): $R_1$=H, n=1, $R_2$=4-chlorophenyl, $R_3$=$R_4$=H, $R_5$=

7.2 g of the purine obtained in Example 46 are placed in 135 ml of 1N HCl. The mixture is heated at 60° C. for 3 h and cooled. The solution is decanted to separate the aqueous phase from the more or less viscous gum formed. The aqueous phase is neutralized with a sodium bicarbonate solution and extracted with chloroform. The organic phases are combined with the gum obtained previously. The mixture is washed with water, dried and concentrated to give 7 g of a cream-colored solid.

The compound is purified by chromatography on silica gel (eluent: chloroform 95%/methanol 5%) to give 3.7 g of β-D-ribofuranuronamido-1-[6-[[2-[1-(4-chlorobenzyl)indol-3-yl]ethyl]amino]-9H-purin-9-yl] -N-cyclopropyl-1-deoxy. Empirical formula: $C_{30}H_{30}ClN_7O_4$. Melting point: 225° C.

The same compound 61 can be obtained by hydrolysis in a formic acid medium (212 ml of a 50% solution) with heating at 70° C. for 75 min.

The compounds of Examples 62 to 75 were prepared according to Example 61:

EXAMPLE 62

β-D-Ribofuranuronamido-1-[6-[[2-[1-(4
-chlorobenzyl)indol-3-yl]ethyl]amino]-9
H-purin-9-yl]-1-deoxy-N-(1,1-dimethyl-2
-hydroxyethyl)

Formula (I): $R_1$=H, n=1, $R_2$=4 -chlorophenyl, $R_3$=$R_4$=H, $R_5$=

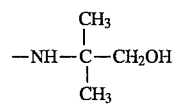

Purified by chromatography twice in succession on silica gel (eluent: chloroform 90%/methanol 10%). Empirical formula: $C_{31}H_{34}ClN_7O_5$. Melting point: 189° C.

EXAMPLE 63

β-D-Ribofuranuronamido-N-cyclopropyl-1
-deoxy-1-[6-[[2-[1-(2-methoxyethyl)indol-3
-yl]ethyl]amino]-9H-purin-9-yl]

Formula (I): $R_1$=H, n=2, $R_2$=methoxy, $R_3$=$R_4$=H, $R_5$=

Purified by chromatography on silica gel (eluent: chloroform 95%/methanol 5%). Empirical formula: $C_{26}H_{31}N_7O_5$. Melting point: 132° C.

EXAMPLE 64

β-D-Ribofuranuronamido-1-[6-[[2-[1
-cyclopentylindol-3-yl]ethyl]amino]-9H-purin-9
-yl]-N-cyclopropyl-1-deoxy Formula (I): $R_1$=H, n=0, $R_2$=cyclopentyl, $R_3$=$R_4$=H, $R_5$=

Purified by chromatography on silica (eluent: chloroform 95%/methanol 5%). Empirical formula: $C_{28}H_{33}N_7O_4$. Melting point: 141° C.

EXAMPLE 65

β-D-Ribofuranuronamido-N-cyclopropyl-1
-deoxy-1-[6-[[2-[1-isopropylindol-3-yl]
-ethyl]amino]-9H-purin-9-yl]

Formula (I): $R_1$=H, n=0, $R_2$=isoproyl, $R_3$=$R_4$=H, $R_5$=

Purified by chromatography on silica gel (eluent: chloroform 90%/methanol 10%). Empirical formula: $C_{26}H_{31}N_7O_4$. Melting point: 135° C.

EXAMPLE 66

β-D-Ribofuranuronamido-N-cyclopropyl-1
-deoxy-1-[6-[[2-[1-(4-methylbenzyl)indol-3
-yl]ethyl]amino]-9H-purin-9-yl]

Formula (I): $R_1$=H, n=1, $R_2$=4 -methylphenyl, $R_3$=$R_4$=H, $R_5$=

Purified by chromatography on silica gel (eluent: chloroform 90%/methanol 10%). Empirical formula: $C_{31}H_{33}N_7O_4 \cdot H_2O$. Melting point: 144° C.

EXAMPLE 67

β-D-Ribofuranuronamido-N-cyclopropyl-1
-deoxy-1-[6-[[2-[1-(3,4
-dimethylbenzyl)indol-3-yl]ethyl]amino]-9H-purin-9-yl]

Formula (I): $R_1$=H, n=1, $R_2$=3,4 -dimethylphenyl, $R_3$=$R_4$=H, $R_5$=

Purified by chromatography on silica gel (eluent: chloroform 95%/methanol 5%). Empirical formula: $C_{32}H_{35}N_7O_4 \cdot H_2O$. Melting point: 134° C.

EXAMPLE 68

β-D-Ribofuranuronamido-N-cyclopropyl-1
-deoxy-1-[6-[[2-[1-(2,5
-dimethylbenzyl)indol-3-yl]ethyl]amino]-9H-purin-9-yl]

Formula (I): $R_1$=H, n=1, $R_2$=2,5 -dimethylphenyl, $R_3$=$R_4$=H, $R_5$=

Purified by chromatography on silica gel (eluent: chloroform 95%/methanol 5%). Empirical formula: $C_{32}H_{35}N_7O_4 \cdot 0.5H_2O$. Melting point: 130° C.

EXAMPLE 69

β-D-Ribofuranuronamido-N-cyclopropyl-1
-deoxy-1-[6-[[2-[1-(2
-N-morpholinoethyl)indol-3-yl]ethyl]amino]-9H-purin-9-yl]

Formula (I): $R_1$=H, n=2, $R_2$=N-morpholino, $R_3$=$R_4$=H, $R_5$=

Purified by chromatography on silica gel (eluent: chloroform 95%/methanol 5%). Empirical formula: $C_{29}H_{36}N_8O_5 \cdot 0.5H_2O$. Melting point: 109°–110° C.

EXAMPLE 70

β-D-Ribofuranuronamido-N-cyclopropyl-1
-deoxy-1-[6-[[2-[1-(2 -N,N-dimethylaminoethyl)
indol-3-yl]ethyl]amino]-9H-purin-9 -yl]

Formula (I): $R_1$=H, n=2, $R_2$= N,N-dimethylamino, $R_3$=$R_4$=H, $R_5$=

Purified by chromatography on silica gel (eluent: chloroform 80%/isopropylamine 20%). Empirical formula: $C_{27}H_{34}N_8O_4 \cdot 0.5H_2O$. Melting point: 112° C.

EXAMPLE 71

β-D-Ribofuranuronamido-N-cyclopropyl-1
-deoxy-1-[6-[[2-[1-(2
-N-piperidinoethyl)indol-3-yl]ethyl]amino]-9H-purin-9-yl]

Formula (I): $R_1$=H, n=2, $R_2$=N-piperidino, $R_3$=$R_4$=H, $R_5$=

Purified by chromatography on silica gel (eluent: chloroform 80%/methanol 20%). Empirical formula: $C_{30}H_{38}N_8O_4$. Melting point: 109° C.

A solution of 11 g of the compound prepared in this way in 100 ml of ethanol is introduced dropwise into a solution of 3.7 g of citric acid in 40 ml of ethanol. The mixture is stirred for 1 h at room temperature. The solid formed is filtered off, washed with ethanol and dried to give 10.6 g of β -D-ribofuranuronamido-N-cyclopropyl-1-deoxy-1-[6-[[2-[1-(2 -N-piperidinoethyl)indol-3-yl]ethyl]amino]-9H-purin-9-yl]citrate. Empirical formula: $C_{30}H_{38}N_8O_4 \cdot C_6H_8O_7$. Melting point: 138° C.

EXAMPLE 72

β-D-Ribofuranuronamido-N-cyclopropyl-1
-deoxy-1-[6-[[2-[1-(2
-N-pyrrolidinoethyl)indol-3-yl]ethyl]amino]-9H-purin-9-yl]

Formula (I): $R_1$=H, n=2, $R_2$= N-pyrrolidino, $R_3$=$R_4$=H, $R_5$=

Purified by chromatography on silica gel (eluent: chloroform 80%/methanol 20%). Empirical formula: $C_{29}H_{36}N_8O_4 \cdot 0.5H_2O$. Melting point: 126° C.

EXAMPLE 73

β-D-Ribofuranuronamido-N-cyclopropyl-1
-deoxy-1-[6-[[2-[1-(3,4
-dichlorobenzyl)indol-3-yl]ethyl]amino]-9H-purin-9-yl]

Formula (I): $R_1$=H, n=1, $R_2$=3,4-dichlorophenyl, $R_3$=$R_4$= H, $R_5$=

Purified by chromatography on silica gel (eluent: chloroform 95%/methanol 5%). Empirical formula: $C_{30}H_{29}Cl_2N_7O_4 \cdot 0.8H_2O$. Melting point: 141° C.

EXAMPLE 74

β-D-Ribofuranuronamido-N-cyclopropyl-1
-deoxy-1-[6-[[2-[1-(pyrid-3
-ylmethyl)indol-3-yl]ethyl]amino]-9H-purin-9-yl]

Formula (I): $R_1$=H, n=1, $R_2$=pyrid-3-yl, $R_3$=$R_4$=H, $R_5$=

Purified by recrystallization from 2-methoxyethanol. Empirical formula: $C_{29}H_{30}N_8O_4 \cdot 0.5CH_3OCH_2CH_2OH$. Melting point: 239° C.

EXAMPLE 75

β-D-Ribofuranuronamido-N-cyclopropyl-1
-deoxy-1-[6-[[2-[1-(naphth-1
-ylmethyl)indol-3-yl]ethyl]amino]-9H-purin-9-yl]

Formula (I): $R_1$=H, n=1, $R_2$=naphth-1-yl, $R_3$=$R_4$=H, $R_5$=

Purified by chromatography on silica gel (eluent: chloroform 95%/methanol 5%) followed by recrystallization from isopropanol. Empirical formula: $C_{34}H_{33}N_7O_4$. Melting point: 168° C.

EXAMPLE 76

$N^6$-[2-[1-(4-Chlorobenzyl)indol-3-yl]ethyl]adenosine

Formula (IV): $R_1$=H, n=1, $R_2$=4-chlorophenyl, $R_3$=$R_4$=H, $R_{12}$= $CH_2OH$, $R_{13}$=$R_{14}$=H 4.5 g of 1-(4-chlorobenzyl)-3-(2-aminoethyl)indole hydrochloride, prepared in Example 29 or 30, are placed in 100 ml of ethanol. 2.1 g of triethylamine and then 2 g of 6-chloroadenosine are added.

The whole is refluxed for 6 h and cooled. The precipitate obtained is filtered off and washed with ethanol and then with ether.

Recrystallization from ethanol gives 2.5 g of $N^6$-[2-[1-(4-chlorobenzyl)indol-3-yl]ethyl]adenosine. Melting point: 181° C.

The compounds of Examples 77 and 78 were prepared according to Example 76:

EXAMPLE 77

$N^6$-[2-[1-Benzylindol-3-yl]ethyl]adenosine

Formula (IV): $R_1$=H, n=1, $R_2$=phenyl, $R_3$=$R_4$=H, $R_{12}$= $CH_2OH$, $R_{13}$=$R_1$=H Purified by recrystallization from ethanol. Melting point: 158° C.

EXAMPLE 78

$N^6$-[2-[1-(2,6-Dichlorobenzyl)indol-3-yl]ethyl]adenosine

Formula (IV): $R_1$=H, n=1, $R_2$=2,6-dichlorophenyl, $R_3$=$R_4$=H, $R_{12}$=$CH_2OH$, $R_{13}$=$R_{14}$=H Purified by recrystallization from ethanol. Melting point: 192° C.

The alcohols of Examples 76, 77 and 78 may be oxidized to the acid by reaction with an oxidizing agent such as chromium trioxide in acetone in the presence of sulfuric acid, or potassium permanganate in water in the presence of ammonia. They will subsequently give the corresponding acid chlorides after reaction with thionyl chloride and then the ribofuranuronamide derivatives of the same type as those of Examples 61, 62, 73 or 75 by reaction with appropriate amines.

The compounds of Examples 79 to 100 were prepared by the procedure of Example 61:

EXAMPLE 79

β-D-Ribofuranuronamido-N-cyclopropyl-1
-deoxy-1-[6-[[2-[1-(pyrid-2
-ylmethyl)indol-3-yl]ethyl]amino]-9H-purin-9-yl]

Formula (I): $R_1$=H, n=1, $R_2$=pyrid-2-yl, $R_3$=$R_4$=H, $R_5$=

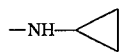

Purified on 3 successive columns (eluent: chloroform 90%/methanol 10%, chloroform 80%/isopropylamine 20% and methylene chloride 90%/methanol 10%, respectively). Empirical formula: $C_{29}H_{30}N_8O_4$. Melting point: 122° C.

EXAMPLE 80

β-D-Ribofuranuronamido-1-[6-[[2-[1-(4
-chlorobenzyl)-5-chloroindol-3-yl]ethyl]
-amino]-9H-purin-9-yl]-N-cyclopropyl-1-deoxy Formula (I): $R_1$=5-Cl, n=1, $R_2$=4-chlorophenyl, $R_3$=$R_4$= H, $R_5$=

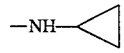

Purified by crystallization from an isopropanol/ether mixture. Empirical formula: $C_{30}H_{29}Cl_2N_7O_4$. Melting point: 154° C.

EXAMPLE 81

β-D-Ribofuranuronamido-1-[6-[[2-[1-(2,5
-dimethylbenzyl)-5-chloroindol-3-yl]ethyl]amino]-9H-
purin-9-yl]-N-cyclopropyl-1-deoxy Formula (I): $R_1$=5-Cl, n=1, $R_2$=2,5-dimethylphenyl, $R_3$=$R_4$=H, $R_5$=

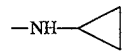

Recrystallization from ethanol with animal charcoal treatment. Empirical formula: $C_{32}H_{34}ClN_7O_4 \cdot 1.1H_2O$. Melting point: 139° C.

EXAMPLE 82

β-D-Ribofuranuronamido-1-[6-[[2-[1-(4
-chlorobenzyl)indol-3-yl]ethyl]amino]-9
H-purin-9-yl]-1-deoxy-N-(2-methoxyethyl)

Formula (I): $R_1$=H, n=1, $R_2$=4-chlorophenyl, $R_3$=$R_4$=H, $R_5$=—NH—$CH_2$—$CH_2$—$OCH_3$ Purified by treatment with hot ethanol. Empirical formula: $C_{30}H_{32}ClN_7O_5$. Melting point: 193° C.

EXAMPLE 83

β-D-Ribofuranuronamido-N-cyclopropyl-1
-deoxy-1-[6-[[2-[1-allylindol-3-yl]ethyl]
-amino]-9H-purin-9-yl]

Formula (I): $R_1$=H, n=1, $R_2$=—HC=$CH_2$, $R_3$=$R_4$=H, $R_5$=

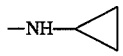

Purified by chromatography on silica gel (eluent: chloroform 90%/methanol 10%). Empirical formula: $C_{26}H_{29}N_7O_4.0.9H_2O$. Melting point: 117° C.

EXAMPLE 84

β-D-Ribofuranuronamido-N-cyclopropyl-1
-deoxy-1-[6-[[2-[1-(prop-2-ynyl)indol-3
-yl]ethyl]amino]-9H-purin-9-yl]

Formula (I): $R_1$=H, n=1, $R_2$=—C≡CH, $R_3$=$R_4$=H, $R_5$=

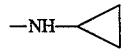

Purified by chromatography on silica gel (eluent: chloroform 90%/methanol 10%). Empirical formula: $C_{26}H_{27}N_7O_4.H_2O$. Melting point: 123° C.

EXAMPLE 85

β-D-Ribofuranuronamido-N-cyclopropyl-1
-deoxy-1-[6-[[2-[1-(2,5-dimethylbenzyl)-5 -methyl
indol-3-yl]ethyl]amino]-9H-purin-9 -yl]

Formula (I): $R_1$=5-$CH_3$, n=1, $R_2$=2,5-dimethylphenyl, $R_3$=$R_4$=H, $R_5$=

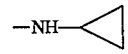

Purified by chromatography on silica gel (eluent: chloroform 90%/methanol 10%). Empirical formula: $C_{33}H_{37}N_7O_4.0.8H_2O$. Melting point: 129° C.

EXAMPLE 86

β-D-Ribofuranuronamido-N-cyclopropyl-1
-deoxy-1-[6-[[2-[1-(2,5-dimethylbenzyl)-5
-methoxyindol-3-yl]ethyl]amino]-9H-purin-9 -yl]

Formula (I): $R_1$=5-$OCH_3$, n=1, $R_2$=2,5 -dimethylphenyl, $R_3$=$R_4$=H, $R_5$=

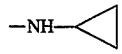

Purified by chromatography on silica gel (eluent: chloroform 90%/methanol 10%). Empirical formula: $C_{33}H_{37}N_7O_5.0.1H_2O$. Melting point: 182° C.

EXAMPLE 87

β-D-Ribofuranuronamido-N-cyclopropyl-1
-deoxy-1-[6-[[2-[1-(2,5-dimethylbenzyl)-2 -methyl
indol-3-yl]ethyl]amino]-9H-purin-9 -yl]

Formula (I): $R_1$=2-$CH_3$, n=1, $R_2$=2,5-dimethylphenyl, $R_3$=$R_4$=H, $R_5$=

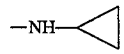

Purified by chromatography on silica gel (eluent: chloroform 90%/methanol 10%). Empirical formula: $C_{33}H_{37}N_7O_4.0.7H_2O$. Melting point: 144° C.

EXAMPLE 88

β-D-Ribofuranuronamido-N-cyclopropyl-1
-deoxy-1-[6-[[2-[1-(4-methoxybenzyl)indol-3
-yl]ethyl]amino]-9H-purin-9-yl]

Formula (I): $R_1$=H, n=1, $R_2$=4-$OCH_3$-phenyl, $R_3$=$R_4$=H, $R_5$=

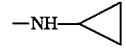

Purified by chromatography on silica gel (eluent: chloroform 90%/methanol 10%). Empirical formula: $C_{31}H_{33}N_7O_5.0.8H_2O$. Melting point: 1340C.

EXAMPLE 89

β-D-Ribofuranuronamido-1-[6-[[2-[1
-cyclopentyl-2-methylindol-3-yl]ethyl]amino]-9
H-purin-9-yl]-N-cyclopropyl-1-deoxy Formula (I): $R_1$=2-$CH_3$, n=0, $R_2$=cyclopentyl, $R_3$=$R_4$=H, $R_5$=

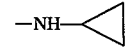

Purified by chromatography on silica gel (eluent: chloroform 90%/methanol 10%). Empirical formula: $C_{29}H_{35}N_7O_4$. Melting point: 140° C.

EXAMPLE 90

β-D-Ribofuranuronamido-N-cyclopropyl-1
-deoxy-1-[6-[[2-[1-(2 -N,N-dimethylaminobenzyl)
indol-3-yl]ethyl]amino]-9H-purin-9 -yl]

Formula (I): $R_1$=H, n=1, $R_2$=2-N,N-dimethylaminophenyl, $R_3$=$R_4$=H, $R_5$=

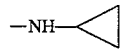

Purified by chromatography on silica gel (eluent: chloroform 90%/methanol 10%). Empirical formula: $C_{32}H_{36}N_8O_4$. Melting point: 128–129° C.

EXAMPLE 91

β-D-Ribofuranuronamido-N-cyclopropyl-1
-deoxy-1-[6-[[2-[1-(3-nitrobenzyl)indol-3
-yl]ethyl]amino]-9H-purin-9-yl]

Formula (I): $R_1$=H, n=1, $R_2$=3-$NO_2$-phenyl, $R_3$=$R_4$=H, $R_5$=

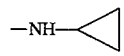

Purified by chromatography twice in succession (eluent: chloroform 90%/methanol 10% and methylene chloride 90%/methanol 10%, respectively). Empirical formula: $C_{30}H_{30}N_8O_6 \cdot 0.3H_2O$. Melting point: 129° C.

EXAMPLE 92

β-D-Ribofuranuronamido-N-cyclopropyl-1
-deoxy-1-[6-[[1-[1-(2,5-dimethylbenzyl)indol-3-yl]
propan-2-yl]amino]-9H-purin-9-yl]

Formula (I): $R_1$=H, n=1, $R_2$=2,5-dimethylphenyl, $R_3$=H, $R_4$= $R_5$=

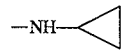

Purified by chromatography on silica gel (eluent: chloroform 90%/methanol 10%). Empirical formula: $C_{33}H_{37}N_7O_4$. Melting point: 135° C.

EXAMPLE 93

β-D-Ribofuranuronamido-N-cyclopropyl-1
-deoxy-1-[6-[[1-[1-cyclopentylindol-3-yl]
-propan-2-yl]amino]-9H-purin-9-yl]

Formula (I): $R_1$=H, n=0, $R_2$=cyclopentyl, $R_{3=H}$, $R_4$=$CH_3$, $R_5$=

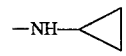

Purified by chromatography on silica gel (eluent: chloroform 90%/methanol 10%). Empirical formula: $C_{29}H_{35}N_7O_4$. Melting point: 130° C.

EXAMPLE 94

β-D-Ribofuranuronamido-N-cyclopropyl-1
-deoxy-1-[6-[[2-[1-(2,5
-dimethylbenzyl)indol-3-yl]propyl]amino]-9H-
purin-9-yl]

Formula (I): $R_1$=H, n=1, $R_2$=2,5-dimethylphenyl, $R_3$=$CH_3$, $R_4$=H,

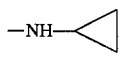

Purified by chromatography on silica gel (eluent: chloroform 95%/methanol 5%). Empirical formula: $C_{33}H_{37}N_7O_4$. Melting point: 137° C.

EXAMPLE 9 5

β-D-Ribofuranuronamido-N-cyclopropyl -1
-deoxy-1-[6-[[2-[1-(2,5-dimethylbenzyl)-2
-phenylindol-3-yl]ethyl]amino]-9H-purin-9 -yl]

Formula (I): $R_1$=2-phenyl, n=1, $R_2$= 2,5-dimethylphenyl, $R_3$=$R_4$= H, $R_5$=

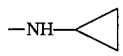

Purified by chromatography on silica gel (eluent: chloroform 90%/methanol 10%). Empirical formula: $C_{38}H_{39}N_7O_4$. Melting point: 136° C.

EXAMPLE 96

β-D-Ribofuranuronamido-N-cyclopropyl-1
-deoxy-1-[6-[[2-[1-(2,5-dimethylbenzyl)-5
-thiomethyl indol-3-yl]ethyl]amino]-9 H-purin-9-yl]

Formula (I): $R_1$=5-$SCH_3$, n=1, $R_2$= 2,5-dimethylphenyl, $R_3$=$R_4$=H, $R_5$=

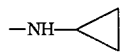

Empirical formula: $C_{33}H_{37}N_7O_4S \cdot 0.8H_2O$. Melting point: 137° C.

EXAMPLE 97

β-D-Ribofuranuronamido-1-[6-[[2-[1-(5
-chlorothien-2-yl)indol-3-yl]ethyl]amino]
-9H-purin-9-yl]-N-cyclopropyl-1-deoxy Formula (I): $R_1$=H, n=1, $R_2$=5 -chlorothien-2-yl, $R_3$=$R_4$= H, $R_5$=

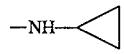

Purified by chromatography on silica gel (eluent: chloroform 90%/methanol 10%). Empirical formula: $C_{28}H_{28}ClN_7O_4S \cdot 1H_2O$. Melting point: 137° C.

EXAMPLE 98

β-D-Ribofuranuronamido-N-cyclopropyl-1-[6 -
[[2-[1-(cyclopropylmethyl)indol-3-yl] -ethyl]amino]-9H-purin-9-yl]-1-deoxy Formula (I): $R_1$=H, n=1, $R_2$= cyclopropyl, $R_3$=$R_{=H}$, $R_5$=

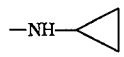

Empirical formula: $C_{27}H_{31}N_7O_4 \cdot 0.5H_2O$. Melting point: 134° C.

The derivatives of Examples 99 to 118 were prepared in the form of amorphous solids by the procedure of EXAMPLE 46 using the appropriate uronamide of formula (III):

EXAMPLE 99

β-D-Ribofuranuronamido-N-cyclopropyl-1
-deoxy-1-[6-[[2-[1-(pyrid-2-ylmethyl)indol-3-
yl]ethyl]amino]-9H-purin-9-yl]-2,3-O-(1
-methylethylidene)

Formula (IV): $R_1$=H, n=1, $R_2$=pyrid-2-yl, $R_3$=$R_4$=H, $R_{12}$=

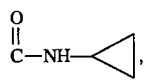

$R_{13}, R_{14}$=

EXAMPLE 100

β-D-Ribofuranuronamido-1-[6-[[2-[1-(4
-chlorobenzyl)-5-chloroindol-3-yl]ethyl]
-amino]-9H-purin-9-yl]-N-cyclopropyl-1
-deoxy-2,3-O-(1-methylethylidene)

Formula (IV): $R_1$=5-Cl, n=1, $R_2$=4 -chlorophenyl, $R_3$=$R_4$=H, $R_{12}$=

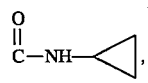

$R_{13}, R_{14}$=

EXAMPLE 101

β-D-Ribofuranuronamido-1-[6-[[2-[1-(2,5
-dimethylbenzyl)-5-chloroindol-3-yl]ethyl]
-amino]-9H-purin-9-yl]-N-cyclopropyl-1
-deoxy-2,3-O-(1-methylethylidene)

Formula (IV): $R_1$=5-Cl, n=1, $R_2$=2,5-dimethylphenyl, $R_3$=$R_4$=H, $R_{12}$=

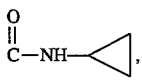

$R_{13}, R_{14}$=

EXAMPLE 102

β-D-Ribofuranuronamido-1-[6-[[2-[1-(4
-chlorobenzyl)indol-3-yl]ethyl]amino]-9
H-purin-9-yl]-1-deoxy-N-(2-methoxyethyl)-2,3-O-
(1-methylethylidene)

Formula (IV): $R_1$=H, n=1, $R_2$=4 -chlorophenyl, $R_3$=$R_4$=H, $R_{12}$=

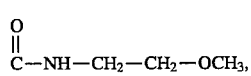

$R_{12}$=

EXAMPLE 103

β-D-Ribofuranuronamido-N-cyclopropyl-1
-deoxy-1-[6-[[2-[1-allylindol-3-yl]ethyl]
-amino]-9H-purin-9-yl]-2,3-O-(1 -methylethylidene)

Formula (IV): $R_1$=H, n=1, $R_2$=ethenyl, $R_3$=$R_4$=H, $R_{12}$=

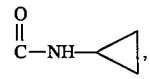

$R_{13}, R_{14}$=

EXAMPLE 104

β-D-Ribofuranuronamido-N-cyclopropyl-1
-deoxy-1-[6-[[2-[1-propargylindol-3-yl]
-ethyl]amino]-9H-purin-9-yl]-2,3-O-(1
-methylethylidene)

Formula (IV): $R_1$=H, n=1, $R_2$=ethynyl, $R_3$=$R_4$=H, $R_{12}$=

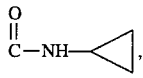

$R_{13},R_{14}$=

EXAMPLE 105

β-D-Ribofuranuronamido-N-cyclopropyl-1
-deoxy-1-[6-[[2-[1-(2,5-dimethylbenzyl)-5
-methylindol-3-yl]ethyl]amino]-9H-purin-9
-yl]-2,3-O-(1-methylethylidene)

Formula (IV): $R_1$=5-$CH_3$, n=1, $R_2$= 2,5-dimethylphenyl, $R_3$= $R_4$=H $R_{12}$=

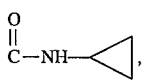

$R_{13},R_{14}$=

EXAMPLE 106

β-D-Ribofuranuronamido-N-cyclopropyl-1
-deoxy-1-[6-[[2-[1-(2,5-dimethylbenzyl)-5
-methoxyindol-3-yl]ethyl]amino]-9H-purin-9
-yl]-2,3-O-(1-methylethylidene)

Formula (IV): $R_1$=5-$OCH_3$, n=1, $R_2$=2,5-dimethylphenyl, $R_3$=$R_4$=H, $R_{12}$=

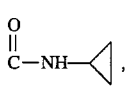

$R_{13},R_{14}$=

EXAMPLE 107

β-D-Ribofuranuronamido-N-cyclopropyl-1
-deoxy-1-[6-[[2-[1-(2,5-dimethylbenzyl)-2
-methylindol-3-yl]ethyl]amino]-9H-purin-9
-yl]-2,3-O-(1-methylethylidene)

Formula (IV): $R_1$=2-$CH_3$, n=1, $R_2$= 2,5-dimethylphenyl, $R_3$= $R_4$=H, $R_{12}$=

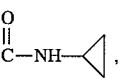

$R_{13},R_{14}$

EXAMPLE 108

β-D-Ribofuranuronamido-N-cyclopropyl-1
-deoxy-1-[6-[[2-[1-(4-methoxybenzyl)indol-3-
yl]ethyl]amino]-9B-purin-9-yl]-2,3-O-(1
-methylethylidene)

Formula (IV): $R_1$=H, n=1, $R_2$=4-$OCH_3$ -phenyl, $R_3$=$R_4$= H, $R_{12}$=

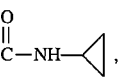

$R_{13},R_{14}$=

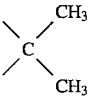

EXAMPLE 109

β-D-Ribofuranuronamido-1-[6-[[2-[1
-cyclopentyl-2-methylindol-3-yl]ethyl]amino]-9
H-purin-9-yl]-N-cyclopropyl-1-deoxy-2,3
-O-(1-methylethylidene)

Formula (IV): $R_1$=2-$CH_3$, n=0, $R_2$= cyclopentyl, $R_3$=$R_4$= H, $R_{12}$=

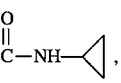

$R_{13},R_{14}$=

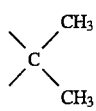

EXAMPLE 110

β-D-Ribofuranuronamido-N-cyclopropyl-1
-deoxy-1-[6-[[2-[1-(2
-N,N-dimethylaminobenzyl)indol-3-yl]ethyl]amino]-
9H-purin-9-yl]-2,3-O-(1-methylethylidene)

Formula (IV): $R_1$=H, n=1, $R_2$=2 -N,N-dimethylaminophenyl, $R_3$= $R_4$=H, $R_{12}$=

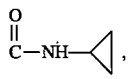, $R_{13}$,$R_{14}$=

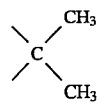

EXAMPLE 111

β-D-Ribofuranuronamido-N-cyclopropyl-1
-deoxy-1-[6-[[2-[1-(3-nitrobenzyl)indol-3
-yl]ethyl]amino]-9H-purin-9-yl]-2,3-O-(1
-methylethylidene)

Formula (IV): $R_1$=H, n=1, $R_2$=3-nitrophenyl, $R_3$=$R_4$=H, $R_{12}$=

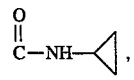, $R_{13}$,$R_{14}$=

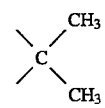

EXAMPLE 112

β-D-Ribofuranuronamido-N-cyclopropyl-1
-deoxy-1-[6-[[1-[1-(2,5
-dimethylbenzyl)indol-3-yl]propan-2-yl]amino]-
9H-purin-9-yl]-2,3-O-(1-methylethylidene)

Formula (IV): $R_1$=H, n=1, $R_2$=2,5-dimethylphenyl, $R_3$=H, $R_4$= $CH_3$, $R_{12}$=

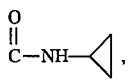, $R_{13}$,$R_{14}$=

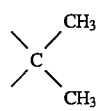

EXAMPLE 113

β-D-Ribofuranuronamido-N-cyclopropyl-1
-deoxy-1-[6-[[1-[1-cyclopentylindol-3-yl]
-propan-2-yl]amino]-9H-purin-9-yl]-2,3-O-
(1-methylethylidene)

Formula (IV): $R_1$=H, n=0, $R_2$=cyclopentyl, $R_3$=H, $R_4$=$CH_3$, $R_{12}$=

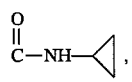, $R_{13}$,$R_{14}$=

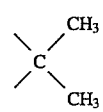

EXAMPLE 114

β-D-Ribofuranuronamido-N-cyclopropyl-1
-deoxy-1-[6-[[2-[1-(2,5
-dimethylbenzyl)indol-3-yl]propyl]amino]-9H-purin-9-yl]
-2,3-O-(1-methylethylidene)

Formula (IV): $R_1$=H, n=1, $R_2$=2,5-dimethylphenyl, $R_3$=$CH_3$, $R_4$=H, $R_{12}$=

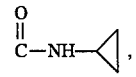, $R_{13}$,$R_{14}$=

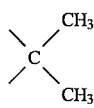

EXAMPLE 115

β-D-Ribofuranuronamido-N-cyclopropyl-1
-deoxy-1-[6-[[2-[1-(2,5-dimethylbenzyl)-2 -phenyl
indol-3-yl]ethyl]amino]-9H-purin-9
-yl]-2,3-O-(1-methylethylidene)

Formula (IV): $R_1$=2-phenyl, n=1, $R_2$= 2,5-dimethylphenyl, $R_3$= $R_4$=H, $R_{12}$=

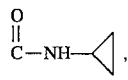

$R_{13}$,$R_{14}$=

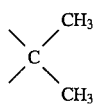

EXAMPLE 116

β-D-Ribofuranuronamido-N-cyclopropyl-1
-deoxy-1-[6-[[2-[1-(2,5-dimethylbenzyl)-5
-thiomethylindol-3-yl]ethyl]amino]-9
H-purin-9-yl]-2,3-O-(1-methylethylidene)

Formula (IV): $R_1$=5-SCH$_3$, n=1, $R_2$= 2,5-dimethylphenyl, $R_3$= $R_4$=H, $R_{12}$=

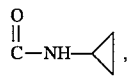

$R_{13}$,$R_{14}$=

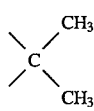

EXAMPLE 117

β-D-Ribofuranuronamido-1-[6-[[2-[1-(5
-chlorothien-2-yl)indol-3-yl]ethyl]amino]
-9H-purin-9-yl]-N-cyclopropyl-1-deoxy-2,3
-O-(1-methylethylidene)

Formula (IV): $R_1$=H, n=1, $R_2$=5-chlorothien-2-yl, $R_3$=$R_4$=H, $R_{12}$=

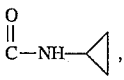

$R_{13}$,$R_{14}$=

EXAMPLE 118

β-D-Ribofuranuronamido-N-cyclopropyl-1-[6
-[[2-[1-(cyclopropylmethyl)indol-3-yl]
-ethyl]amino]-9H-purin-9-yl]-1-deoxy-2,3
-O-(1-methylethylidene)

Formula (IV): $R_1$=H, n=1, $R_2$=cyclopropyl, $R_3$=$R_4$=H, $R_{12}$=

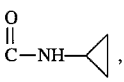

$R_{13}$,$R_{14}$=

The following compounds of Examples 119 to 138 were prepared by one of the procedures of Examples 29 or 30:

EXAMPLE 119

3-(2-Aminoethyl)-5-chloro-(2,5
-dimethylbenzyl)indole

Formula (II): $R_1$=5-Cl, n=1, $R_2$=2,5 -dimethylphenyl, $R_3$=$R_4$=H

A brown oil purified by chromatography on silica gel (eluent: chloroform 95%/isopropylamine 5%).

EXAMPLE 120

3-(2-Aminoethyl)-1-allylindole

Formula (II): $R_1$=H, n=1, $R_2$=ethenyl, $R_3$=$R_4$=H

A brown oil purified by chromatography on silica gel (eluent: chloroform 95%/isopropylamine 5%).

EXAMPLE 121

3-(2-Aminoethyl)-1-(pyrid-2-ylmethyl)indole

Formula (II): $R_1$=H, n=1, $R_2$=pyrid-2-yl, $R_3$=$R_4$=H

Purified by chromatography on silica gel (eluent: $CHCl_3$ 95%/isopropylamine 5%). Melting point: 237° C.

EXAMPLE 122

3-(2-Aminoethyl)-5-chloro-1-(4-chlorobenzyl)indole

Formula (II): $R_1$=5-Cl, n=1, $R_2$=4-chlorophenyl, $R_3$=$R_4$=H

The hydrochloride purified by recrystallization from ethanol. Melting point: 204° C.

EXAMPLE 123

3-(2-Aminoethyl)-1-propargylindole

Formula (II): $R_1$=H, n=1, $R_2$=ethynyl, $R_3$=$R_4$=H

A brown oil purified by chromatography on silica gel (eluent: chloroform 95%/isopropylamine 5%).

EXAMPLE 124

3-(2-Aminoethyl)-1-(2,5-dimethylbenzyl)-5-methylindole

Formula (II): $R_1$=5-$CH_3$, n=1, $R_2$=2,5-dimethylphenyl, $R_3$=$R_4$=H

The hydrochloride purified by crystallization from ether. Melting point: 198° C.

EXAMPLE 125

3-(2-Aminoethyl)-1-(2,5-dimethylbenzyl)-5-methoxyindole

Formula (II): $R_1$=5-$OCH_3$, n=1, $R_2$=2,5-dimethylphenyl, $R_3$=$R_4$=H

An amorphous white solid purified by chromatography on silica gel (eluent: chloroform 95%/methanol 5%).

EXAMPLE 126

3-(2-Aminoethyl)-1-(2,5-dimethylbenzyl)-2-methylindole

Formula (II): $R_1$=2-$CH_3$, n=1, $R_2$=2,5-dimethylphenyl, $R_3$=$R_4$=H

The hydrochloride purified by crystallization from ether. Melting point: 250° C.

EXAMPLE 127

3-(2-Aminoethyl)-1-(4-methoxybenzyl)indole

Formula (II): $R_1$=H, n=1, $R_2$=4$OCH_3$-phenyl, $R_3$=$R_4$=H

A brown oil purified by chromatography on silica gel (eluent: chloroform 95%/isopropylamine 5%).

EXAMPLE 128

3-(2-Aminoethyl)-1-cyclopentyl-2-methylindole

Formula (II): $R_1$=2-$CH_3$, n=0, $R_2$=cyclopentyl, $R_3$$R_4$=H

A crude orange oil used as such in the next step.

EXAMPLE 129

3-(2-Aminoethyl)-2-phenylindole

Formula (V): $R_1$=2-phenyl, $R_3$=$R_4$=H

The hydrochloride purified by crystallization from isopropanol. Melting point: 266° C.

EXAMPLE 130

3-(2-Aminoethyl)-1-(2,5-dimethylbenzyl)-2-phenylindole

Formula (II): $R_1$=2-phenyl, n=1, $R_2$=2,5-dimethylphenyl, $R_3$=$R_4$=H

A brown oil purified by chromatography on silica gel (eluent: chloroform 95%/isopropylamine 5%).

EXAMPLE 131

3-(2-Aminoethyl)-1-(2-N,N-dimethylaminobenzyl)indole

Formula (II): $R_1$=H, n=1, $R_2$=2-N,N-dimethylaminophenyl, $R_3$=$R_4$=H

A brown oil purified by chromatography on silica gel (eluent: chloroform 95%/isopropylamine 5%).

EXAMPLE 132

3-(2-Aminoethyl)-1-(3-nitrobenzyl)indole

Formula (II): $R_1$=H, n=1, $R_2$=3-$NO_2$-phenyl, $R_3$=$R_4$=H

A brown oil purified by chromatography on silica gel (eluent: chloroform 95%/isopropylamine 5%).

EXAMPLE 133

3-(2-Aminopropyl)-1-(2,5-dimethylbenzyl)indole

Formula (II): $R_1$=H, n=1, $R_2$=2,5-dimethylphenyl, $R_3$=H, $R_4$=$CH_3$

A white solid crystallized from isopropyl ether. Melting point: 87° C.

EXAMPLE 134

3-(2-Aminopropyl)-1-cyclopentylindole

Formula (II): $R_1$=H, n=0, $R_2$=cyclopentyl, $R_3$=H, $R_4$=$CH_3$

A crude orange oil used as such in the next step.

EXAMPLE 135

3-(Aminopropan-2-yl)-1-(2,5-dimethylbenzyl)indole

Formula (II): $R_1$=H, n=1, $R_2$=2,5-dimethylphenyl, $R_3$=$CH_3$, $R_4$=H

An oil purified by chromatography on silica gel (eluent: chloroform 95%/isopropylamine 5%). The hydrochloride crystallized from isopropanol. Empirical formula: $C_{20}H_{24}N_2.HCl$. Melting point: 178° C.

EXAMPLE 136

3-(Aminoethyl)-1-[(5-chlorothien-2-yl)methyl] indole

Formula (II): $R_1$=H, n=1, $R_2$=5-chlorothien-2-yl, $R_3$=$R_4$=H

A brown oil purified by chromatography on silica gel (eluent: chloroform 95%/isopropanol 5%).

EXAMPLE 137

3-(Aminoethyl)-1-(cyclopropylmethyl)indole

Formula (II): $R_1$=H, n=1, $R_2$=cyclopropyl, $R_3$=$R_4$=H

A brown oil purified by chromatography on silica gel (eluent: chloroform 95%/isopropylamine 5%).

EXAMPLE 138

3-(2-Aminoethyl)-1-(2,5-dimethylbenzyl)-5-thiomethylindole

Formula (II): $R_1$=5-$SCH_3$, n=1, $R_2$= 2,5-dimethylphenyl, $R_3$= $R_4$=H

A brown oil purified by chromatography on silica gel (eluent: chloroform 95%/isopropylamine 5%).

The nitrovinylindoles of Examples 139 to 143 were prepared by the procedure of Example 17:

EXAMPLE 139

1-(2,5-Dimethylbenzyl)-2-methyl-3-(2-nitrovinyl)indole

Formula (IX): $R_1$=2-$CH_3$, n=1, $R_2$= 2,5-dimethylphenyl, $R_3$= $R_4$=H

An orange solid used as such in the next step. Melting point: 180° C.

EXAMPLE 140

1-(Cyclopentyl)-2-methyl-3-(2-nitrovinyl)indole

Formula (IX): $R_1$=2-$CH_3$, n=0, $R_2$= cyclopentyl, $R_3$=$R_4$=H

An orange oil purified by chromatography on silica gel (eluent: chloroform).

EXAMPLE 141

2-Phenyl-3-(2-nitrovinyl)indole

Formula (IX): $R_1$=2-phenyl, n=0, $R_2$= H, $R_3$=$R_4$=H

An orange solid used as such in the next step. Melting point: 180° C.

The compounds of Examples 142 and 143 are obtained by the procedure of Example 17 using nitroethane in place of nitromethane:

EXAMPLE 142

1-(2,5-Dimethylbenzyl)-3-(2-methyl-2-nitrovinyl)indole

Formula (IX): $R_1$=H, n=1, $R_2$=2,5 -dimethylphenyl, $R_3$=H, $R_4$= $CH_3$

A yellow solid crystallized from water. Melting point: 160° C.

EXAMPLE 143

1-Cyclopentyl-3-(2-methyl-2-nitrovinyl)indole

Formula (IX): $R_1$=H, n=0, $R_2$=cyclopentyl, $R_3$=H $R_4$=$CH_3$

A yellow solid crystallized from isopropanol. Melting point: 135° C.

The following products of Examples 144 to 146 were prepared by the method of Example 5 starting from appropriately substituted 3-formylindoles:

Example 144

1-(2,5-Dimethylbenzyl)-3-formyl-2-methylindole

Formula (VIII): $R_1$=2-$CH_3$, n=1, $R_2$= 2,5-dimethylphenyl

A yellow solid crystallized from ether and used as such in the next step. Melting point: 155° C.

EXAMPLE 145

1-(Cyclopentyl)-3-formyl-2-methylindole

Formula (VIII): $R_1$=2-$CH_3$, n=0, $R_2$= cyclopentyl

A brown oil purified by chromatography on silica gel (eluent: chloroform 95%/methanol 5%).

EXAMPLE 146

3-Formyl-2-phenylindole

Formula (VIII): $R_1$=2-phenyl, n=0, $R_2$=H

A cream-colored solid used as such in the next step and obtained by the procedure described in J. Med. Chem. (1964), 7, 735. Melting point: 253° C.

The following compound of Example 147 was prepared by the procedure of Example 1 using 2-methoxyethylamine:

EXAMPLE 147

β-D-Ribofuranuronamido-1-(6-chloro-9 H-purin-9-yl)-1-deoxy-N-(2-methoxyethyl)-2,3-O-(1-methylethylidene)

Formula (III): X=Cl, $R_{12}$=

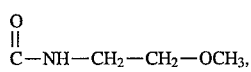

$R_{13}$,$R_{14}$=

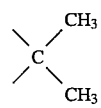

A brown oil purified by chromatography on silica gel (eluent: chloroform 95%/methanol 5%).

The compound of Example 148 was prepared in the form of an amorphous solid by the procedure of Example 46 using the uronamide of Example 2:

EXAMPLE 148

β-D-Ribofuranuronamido-1-deoxy-1-[6-[[2-[1-(2,5-dimethylbenzyl)indol-3-yl]ethyl]amino]-9H-purin-9-yl]-N-ethyl-2,3-O-(1-methylethylidene)

Formula (IV): $R_1=H$, $n=1$, $R_2=$2,5-dimethylphenyl, $R_3=R_4=H$, $R_{12}=$ $$\overset{O}{\underset{\|}{C}}-NH-CH_2-CH_3,$$

$R_{13}, R_{14}=$

The compound of Example 149 was prepared by the method of Example 61:

EXAMPLE 149

β-D-Ribofuranuronamido-1-deoxy-1-[6-[[2-[1-(2,5-dimethylbenzyl)indol-3-yl]ethyl]amino]-9H-purin-9-yl]-N-ethyl Formula (I): $R_1=H$, $n=1$, $R_2=$2,5-dimethylphenyl, $R_3=R_4=H$, $R_5=-NH-CH_2-CH_3$ Empirical formula: $C_{31}H_{35}N_4 \cdot 0.4H_2O$. Melting point: 133° C.

PHARMACOLOGY

The pharmacological activity of the products of the Examples was evaluated by two different approaches: binding to adenosine receptors and/or demonstration of analgesic activity by the phenylbenzoquinone test.

I Procedure

1. Binding to adenosine receptors

Principle

The affinity of the products of the Examples for the rat central $A_1$ and $A_2$ adenosinergic receptors is determined by the competitive technique using a radioactive ligand specifically bound either to the $A_1$ receptors ([$^3$H] PIA) or to the $A_2$ receptors ([$^3$H] NECA).

Method

Method of studying the $A_1$ receptors

Membrane preparation

After the animal has been sacrificed by decapitation, the brain is quickly removed and washed in cold isotonic solution. The two hemispheres are separated and weighed and each of them is introduced into a polyallomer tube containing 25 volumes of cold homogenization buffer. Homogenization is effected using an Ultra-Turrax for 30 seconds (3 times 10 seconds with 10-second intervals, 70% of the maximum speed). The ground material obtained is centrifuged at 1000 g (≈ 3000 rpm) for 10 minutes at 4° C.

The supernatant is centrifuged again at 48,000 g (≈20,000 rpm) for 20 minutes at 4° C.

When this step is complete, the residue is taken up with 4 volumes of homogenization buffer, resuspended using a Vortex and homogenized with the Ultra-Turrax. Adenosine deaminase is then added at a rate of 1 U/ml, i.e. 1 μl/ml of homogenate, using a 10 μl Hamilton syringe.

After this treatment, the homogenate is shaken for 30 minutes at room temperature and then centrifuged at 80,000 g (≈20,000 rpm) for 30 minutes at 4° C.

The residue obtained is resuspended in 10 volumes of homogenization buffer and passed through the Ultra-Turrax for 20 seconds (2 times 10 seconds with a 10-second interval, 70% of the maximum speed).

The homogenate prepared in this way is used for the competitive tests. It is kept at 4° C. if the studies take place the same day, or stored at −20° C. in the form of 10 ml aliquots.

Competitive test

After the homogenate has been thawed at room temperature, it is passed through a Potter mill (6 manual to-and-fro movements, speed 6), diluted to 2/5 in incubation buffer and placed in a water bath thermostated at 4° C., with shaking, until the end of the experiment.

50 μl of [$^3$H] PIA at 100 nM, i.e. 2.5 nM in the final reaction medium allowing for the 1/40 dilution, and 50 μl of the product of the Example at the concentrations considered ($10^{-1}$M and $10^{-7}$M) are introduced into the reaction tubes. The reaction is initiated by the addition of 1 ml of homogenate and 900 μl of incubation buffer. The procedure is identical for all the beta-blockers studied.

The tubes are shaken and incubated in a water bath at 20° C. for 30 minutes. When the incubation is complete, the contents of the tubes are filtered on Whatman GF/B paper. Each tube is washed twice with 2 ml of rinsing buffer and then the filters themselves are rinsed with 3 ml of this same buffer.

The filters are then transferred to counting flasks and 10 ml of liquid scintillator (Ready Solv HP/b, Beckman) are added.

After they have been shaken, the flasks are stored in a refrigerator overnight and the radio-activity is then determined in a liquid scintillation counter.

3 tests are performed for each concentration studied. The non-specific binding of the [$^3$H] PIA is assessed by measuring the amount of radioactivity retained on the filter in the presence of $10^{-5}$M phenylisopropyladenosine (PIA). The value of the non-specific binding is systematically subtracted from that of the tests.

Method of studying the $A_2$ receptors Membrane preparation

After decapitation of the animal, the brain is quickly removed and washed in cold isotonic solution. The two hemispheres are separated and the striatum is removed from each of them (Bruns et al., 1986), weighed and introduced into a polyallomer tube containing 10 volumes of cold homogenization buffer. The tissue is homogenized with an Ultra-Turrax for 30 seconds (3 times 10 seconds with 10-second intervals, 70% of the maximum speed). The ground material is centrifuged at 50,000 g (≈20,500 rpm) for 10 minutes at 4° C.

The residue obtained is resuspended in 10 volumes of homogenization buffer using a Vortex and homogenized with the Ultra-Turrax (5 to 10 seconds, 70% of the maximum speed).

Adenosine deaminase is then added at a rate of 1 U/ml, i.e. 1 μl/ml of homogenate, using a 10 μl Hamilton syringe. The homogenate treated in this way is shaken at room temperature for 30 minutes.

When the incubation is complete, the homogenate is centrifuged at 50,000 g (≈20,500 rpm) for 10 minutes at 4° C.

The residue is taken up with 5 volumes of cold homogenization buffer and passed through the Ultra-Turrax (2 times 10 seconds with a 10-second interval, 70% of the maximum speed) and the homogenate prepared in this way is finally frozen at −70° C. Competitive test After the homogenate has been thawed at room temperature, 15 volumes of incubation buffer are added. The homogenate is shaken on a Vortex, passed through a Potter mill (6 to-and-fro movements, speed 6), diluted to 1/10 in incubation buffer and finally placed in a water bath thermostated at 4° C., with shaking, until the end of the experiment.

50 µl of [$^3$H] NECA at 160 nM, i.e. 4 nM in the final reaction medium allowing for the 1/40 dilution, and 50 µl of the product of the Example at the concentrations considered ($10^{-5}$M and $10^{-7}$M) are introduced into the reaction tubes. The reaction is initiated by the addition of 1 ml of homogenate and 900 µl of incubation buffer. The procedure is similar for all the compounds studied.

The tubes are shaken and incubated in a water bath at 25° C. for 60 minutes. When the incubation is complete, the contents of the tubes are filtered on Whatman GF/B paper. Each tube is washed twice with 2 ml of rinsing buffer and then the filters themselves are rinsed with 3 ml of this same buffer before being transferred to counting flasks.

10 ml of liquid scintillator (Ready Solv HP/b, Beckman) are added to all the flasks. These are shaken and stored in a refrigerator overnight. The radioactivity is determined in a liquid scintillation counter.

3 tests are performed for each concentration studied. The non-specific binding of the [$^3$H] NECA is determined by measuring the amount of radioactivity retained on the filter in the presence of 5 µM N-ethylcarboxamidoadenosine (NECA). The value of the non-specific binding is systematically subtracted from that of the tests.

Treatment of the data

The results are expressed for each product in the form of the percentage displacement (n=3) of the labeled radioligand at concentrations of $10^{-5}$M and $10^{-7}$M.

2. Phenylbenzoquinone test

Method

The intraperitoneal injection of phenylbenzoquinone causes twisting and stretching movements in mice. Analgesics prevent or reduce this syndrome, which can be considered as the exteriorization of diffuse abdominal pain.

A 0.02% solution of phenylbenzoquinone in water is administered in a volume of 1 ml/100 g.

The products of the Examples are administered orally one hour before the injection of phenylbenzoquinone.

The stretching and twisting movements are counted for each mouse over an observation period of 5 minutes.

II Results

The results of the experiments demonstrate the affinity of the products of the Examples for adenosine receptors and their analgesic properties are presented in Tables 1 and 2 respectively.

TABLE 1

| | % displacement of the labeled ligand | | | |
|---|---|---|---|---|
| | A1 | | A2 | |
| Product of | 1E-5M | 1E-7M | 1E-5M | 1E-7M |
| Example 61 | 98 | 47 | 91 | 30 |

TABLE 1-continued

| | % displacement of the labeled ligand | | | |
|---|---|---|---|---|
| | A1 | | A2 | |
| Product of | 1E-5M | 1E-7M | 1E-5M | 1E-7M |
| Example 63 | 98 | 61 | 90 | 19 |
| Example 64 | 96 | 21 | 90 | 28 |
| Example 65 | 87 | 4 | 91 | 14 |
| Example 66 | 97 | 37 | 89 | 21 |
| Example 67 | 96 | 29 | 83 | 13 |
| Example 68 | 93 | 26 | 84 | 9 |
| Example 69 | 93 | 63 | 90 | 12 |
| Example 70 | 100 | 91 | 94 | 44 |
| Example 71 (citrate) | 99 | 91 | 96 | 44 |
| Example 71 (base) | 99 | 94 | 92 | 46 |
| Example 85 | 100 | 50 | 71 | 3 |
| Example 86 | 100 | 16 | 91 | 17 |
| Example 87 | 56 | 5 | 60 | 7 |
| Example 92 | 96 | 21 | 84 | 9 |
| Example 93 | 96 | 45 | 85 | 22 |

TABLE 2

| Product of | Phenylbenzoquinone test 50% inhibitory dose mg/kg p.o. |
|---|---|
| Example 61 | 0.90 |
| Example 63 | 10 |
| Example 64 | 0.3 |
| Example 65 | 0.3 |
| Example 66 | 3 |
| Example 67 | 3 |
| Example 68 | 2.4 |
| Example 71 (citrate) | 7.3 |
| Example 85 | 0.9 |
| Example 86 | ≈60 |
| Example 87 | 1.2 |
| Example 92 | 3.6 |
| Example 93 | 2 |

III Toxicology

The tolerance of the products of the Examples was assessed in rats after oral administration. It was found to be good up to a dose of 100 mg/kg.

IV Conclusion

The products of the Examples described in the present invention possess particularly valuable analgesic properties, whose original mechanism of action results from an interaction with adenosine receptors.

What is claimed is:

1. An adenosine derivative of general formula (I):

Formula (I)

in which:

$R_1$ is a hydrogen atom, a halogen atom, a $C_1$–$C_6$ alkyl radical, a $C_1$–$C_6$ O-alkyl radical, a $C_1$–$C_6$ S-alkyl radical or a phenyl radical located in the 2-, 4-, 5-, 6- or 7-position of the indole;

n is an integer from 0 to 4;

$R_2$ is a $C_1$–$C_6$ alkyl radical, a $C_1$–$C_6$ alkenyl radical, $C_1$–$C_6$ alkynyl radical, a $C_3$–$C_7$-cycloalkyl radical or $C_1$–$C_6$ O-alkyl radical;

a phenyl or naphthyl radical which is unsubstituted or substituted by one to four identical or different substituents selected from the group consisting of a halogen atom, a nitro, $C_1$–$C_6$ alkyl, $C_1$–$C_6$ O-alkyl or $C_1$–$C_6$ S-alkyl group and a group —$NR_7R_8$, $R_7$ and $R_8$ being the hydrogen atom or a $C_1$–$C_6$ alkyl radical;

a heterocyclic radical selected from the group consisting of pyridine and thiophene which is unsubstituted or substituted by one to four identical or different substituents selected from the group consisting of a halogen atom and a nitro, $C_1$–$C_6$ alkyl, $C_1$–$C_6$ O-alkyl and $C_1$–$C_6$ S-alkyl group;

or, when n is equal to 2, 3 or 4, a group —$NR_9R_{10}$, $R_9$ and $R_{10}$ simultaneously being a $C_1$–$C_6$ alkyl radical or forming, together with the nitrogen atom to which they are attached, a heterocycle selected from the group consisting of morpholine, piperidine and pyrrolidine;

$R_3$ and $R_4$ which are identical or different, are a hydrogen atom or a $C_1$–$C_6$ alkyl radical; and $R_5$ is a group —$NHR_{11}$, $R_{11}$ being a $C_1$–$C_6$ alkyl radical, a $C_3$–$C_7$-cycloalkyl radical, a $C_1$–$C_6$ alkyl chain possessing an alcohol or ether functional group, or a group —$(CH)_n$—$NR_9R_{10}$, n, $R_9$ and $R_{10}$ being as defined above.

2. A derivative of general formula (I) according to claim 1 wherein:

$R_1$ is a hydrogen atom, a halogen atom, a $C_1$–$C_6$ alkyl radical, a $C_1$–$C_6$ O-alkyl radical, a $C_1$–$C_6$ S-alkyl radical or a phenyl radical located in the 2- or 5-position of the indole;

n is an integer equal to 0, 1 or 2;

$R_2$ is a $C_1$–$C_6$ alkyl radical, a $C_1$–$C_6$ alkenyl radical, a $C_1$–$C_6$ alkynyl radical, a $C_3$–$C_7$-cycloalkyl radical or a $C_1$–$C_6$ O-alkyl radical;

a phenyl or naphthyl radical which is unsubstituted or substituted by one or two identical or different substituents selected from the group consisting of a halogen atom, a nitro, $C_1$–$C_6$ alkyl and $C_1$–$C_6$ O-alkyl group and a group —$NR_7R_8$, $R_7$ and $R_8$ being the hydrogen atom or a $C_1$–$C_6$ alkyl radical;

a heterocyclic radical selected from the group consisting of pyridine and thiophene which is unsubstituted or substituted by a halogen atom;

or, when n=2, a group —$NR_9R_{10}$, $R_9$ and $R_{10}$ simultaneously being a $C_1$–$C_6$ alkyl radical or forming, together with the nitrogen atom to which they are attached, a heterocycle selected from morpholine, piperidine and pyrrolidine;

$R_3$ and $R_4$, which are identical or different, are a hydrogen atom or a $C_1$–$C_6$ alkyl radical; and $R_5$, is a group —$NHR_{11}$, $R_{11}$ being a $C_1$–$C_6$ alkyl radical, a $C_3$–$C_7$-cycloalkyl radical or a $C_1$–$C_6$ alkyl chain possessing an alcohol or ether functional group.

3. A derivative according to claim 1 or claim 2 wherein $R_1$ is a hydrogen atom or a radical selected from methyl or methoxy.

4. A derivative according to claim 1 or claim 2 wherein n is 0, 1 or 2.

5. A derivative according to claim 1 or claim 2 wherein $R_2$ is a radical selected from the group consisting of methoxy, cyclopentane, isopropyl, 2,5-dimethylphenyl and piperidine.

6. A derivative according to claim 1 or claim 2 wherein $R_3$ is a hydrogen atom.

7. A derivative according to claim 1 or claim 2 wherein $R_4$ is a hydrogen atom or a methyl radical.

8. A derivative according to claim 1 or claim 2 wherein $R_5$ is an N-cyclopropylamine radical.

9. A derivative according to claim 1 or claim 2 which is selected from the group consisting of following derivatives:

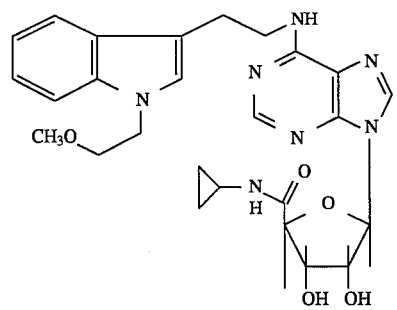

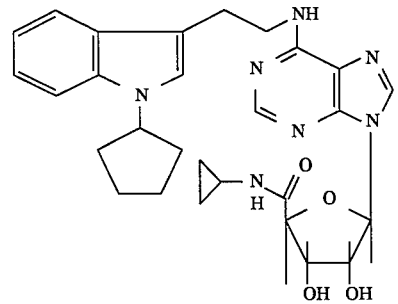

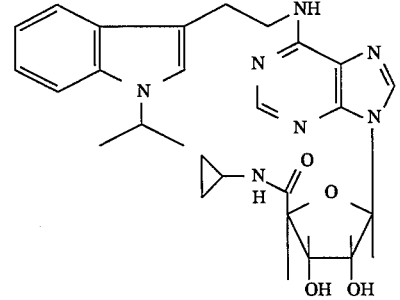

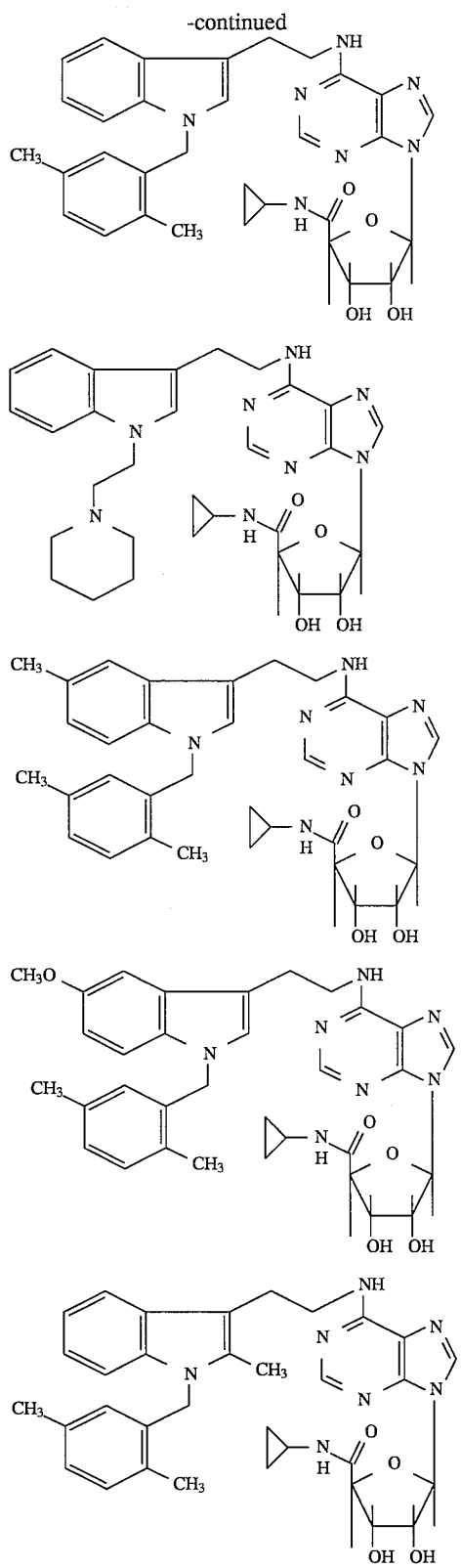
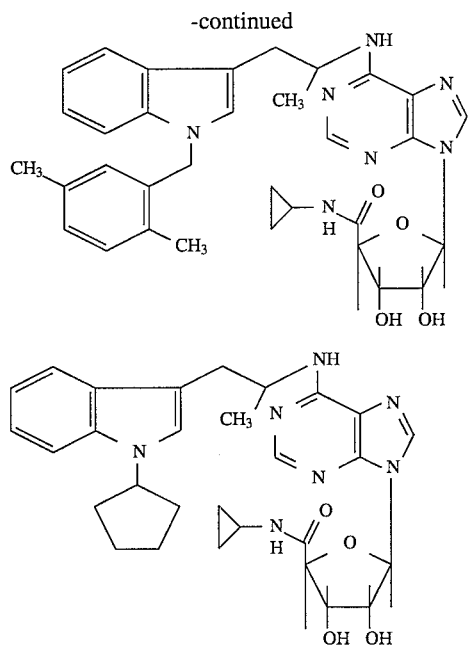

10. A method for preparing a compound of formula (I):

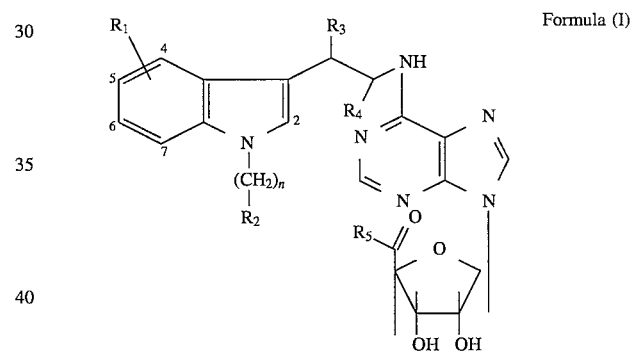

Formula (I)

in which:

$R_1$ is a hydrogen atom, a halogen atom, a $C_1$–$C_6$ alkyl radical, a $C_1$–$C_6$ O-alkyl radical, a $C_1$–$C_6$ S-alkyl radical or a phenyl radical located in the 2-, 4-, 5-, 6- or 7-position of the indole;

n is an integer from 0 to 4;

$R_2$ is a $C_1$–$C_6$ alkyl radical, a $C_1$–$C_6$ alkenyl radical, $C_1$–$C_6$ alkynyl radical, a $C_3$–$C_7$-cycloalkyl radical or $C_1$–$C_6$ O-alkyl radical;

a phenyl or naphthyl radical which is unsubstituted or substituted by one to four identical or different substituents selected from the group consisting of a halogen atom, a nitro, $C_1$–$C_6$ alkyl, $C_1$–$C_6$ O-alkyl or $C_1$–$C_6$ S-alkyl group and a group —$NR_7R_8$, $R_7$ and $R_8$ being the hydrogen atom or a $C_1$–$C_6$ alkyl radical;

a heterocyclic radical selected from the group consisting of pyridine and thiophene which is unsubstituted or substituted by one to four identical or different substituents selected from the group consisting of a halogen atom and a nitro, $C_1$–$C_6$ alkyl, $C_1$–$C_6$ O-alkyl and $C_1$–$C_6$ S-alkyl group;

or, when n is equal to 2, 3 or 4, a group —$NR_9R_{10}$, $R_9$ and $R_{10}$ simultaneously being a $C_1$–$C_6$ alkyl radical or forming, together with the nitrogen atom to which they are attached, a heterocycle selected from the group consisting of morpholine, piperidine and pyrrolidine;

$R_3$ and $R_4$ which are identical or different, are the hydrogen atom or a $C_1$–$C_6$ alkyl radical; and $R_5$ is a group —$NHR_{11}$, $R_{11}$ being a $C_1$–$C_6$ alkyl radical, a $C_3$–$C_7$-cycloalkyl radical, a $C_1$–$C_6$ alkyl chain possessing an alcohol or ether functional group, or a group —$(CH)_n$—$NR_9R_{10}$, n, $R_9$ and $R_{10}$ being as defined above, comprising reacting an amine of the formula:

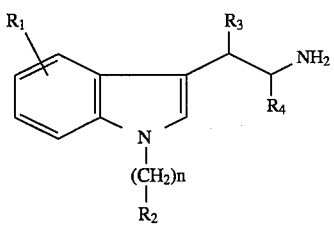

in which $R_1$, $R_2$, $R_3$ and $R_4$ and n are as defined hereinabove, with a 6-halogenopurine riboside of the formula:

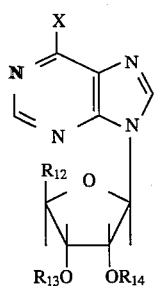

in which X is a halogen atom, $R_{12}$ is a group $COR_5$, $R_5$ being as defined hereinabove, or the $CH_2OH$ group, and $R_{13}$ and $R_{14}$ are protecting groups or together form another protecting group, in a solvent in the presence of a base or in the presence of two equivalents of the amine, at a temperature of between 20° and 140° C., and deprotecting the $OR_{13}$ and $OR_{14}$ groups, in a basic medium with an ammoniacal alcohol solution, or in an acid medium with a normal hydrochloric acid solution or a formic acid solution, at a temperature of 0° to 70° C.

11. A pharmaceutical composition which comprises at least one compound of formula (I):

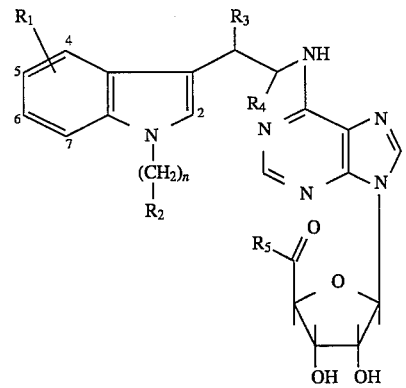

in which:

$R_1$ is a hydrogen atom, a halogen atom, a $C_1$–$C_6$ alkyl radical, a $C_1$–$C_6$ O-alkyl radical, a $C_1$–$C_6$ S-alkyl radical or a phenyl radical located in the 2-, 4-, 5-, 6- or 7-position of the indole;

n is an integer from 0 to 4;

$R_2$ is a $C_1$–$C_6$ alkyl radical, a $C_1$–$C_6$ alkenyl radical, $C_1$–$C_6$ alkynyl radical, a $C_3$–$C_7$-cycloalkyl radical or $C_1$–$C_6$ O-alkyl radical;

a phenyl or naphthyl radical which is unsubstituted or substituted by one to four identical or different substituents selected from the group consisting of a halogen atom, a nitro, $C_1$–$C_6$ alkyl, $C_1$–$C_6$ O-alkyl or $C_1$–$C_6$ S-alkyl group and a group —$NR_7R_8$, $R_7$ and $R_8$ being the hydrogen atom or a $C_1$–$C_6$ alkyl radical;

a heterocyclic radical selected from the group consisting of pyridine and thiophene which is unsubstituted or substituted by one to four identical or different substituents selected from the group consisting of a halogen atom and a nitro, $C_1$–$C_6$ alkyl, $C_1$–$C_6$ O-alkyl and $C_1$–$C_6$ S-alkyl group;

or, when n is equal to 2, 3 or 4, a group —$NR_9R_{10}$, $R_9$ and $R_{10}$ simultaneously being a $C_1$–$C_6$ alkyl radical or forming, together with the nitrogen atom to which they are attached, a heterocycle selected from the group consisting of morpholine, piperidine and pyrrolidine;

$R_3$ and $R_4$ which are identical or different, are the hydrogen atom or a $C_1$–$C_6$ alkyl radical; and $R_5$ is a group —$NHR_{11}$, $R_{11}$ being a $C_1$–$C_6$ alkyl radical, a $C_3$–$C_7$-cycloalkyl radical, a $C_1$–$C_6$ alkyl chain possessing an alcohol or ether functional group, or a group —$(CH)_n$—$NR_9R_{10}$, n, $R_9$ and $R_{10}$ being as defined above, or a pharmaceutically acceptable addition salt thereof, in combination with a pharmaceutically acceptable excipient, vehicle or carrier.

12. A pharmaceutical composition with analogesic activity which comprises a pharmaceutically effective amount of at least one compound of formula (I):

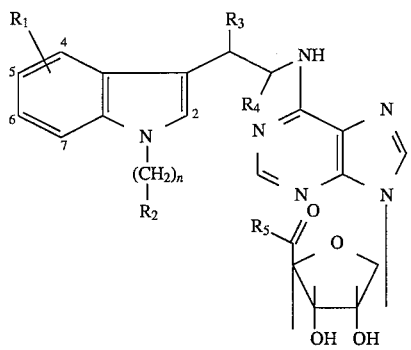

in which:

R$_1$ is a hydrogen atom, a halogen atom, a C$_1$–C$_6$ alkyl radical, a C$_1$–C$_6$ O-alkyl radical, a C$_1$–C$_6$ S-alkyl radical or a phenyl radical located in the 2-, 4-, 5-, 6- or 7-position of the indole;

n is an integer from 0 to 4;

R$_2$ is a C$_1$–C$_6$ alkyl radical, a C$_1$–C$_6$ alkenyl radical, C$_1$–C$_6$ alkynyl radical, a C$_3$–C$_7$-cycloalkyl radical or C$_1$–C$_6$ O-alkyl radical;

a phenyl or naphthyl radical which is unsubstituted or substituted by one to four identical or different substituents selected from the group consisting of a halogen atom, a nitro, C$_1$–C$_6$ alkyl, C$_1$–C$_6$ O-alkyl or C$_1$–C$_6$ S-alkyl group and a group —NR$_7$R$_8$, R$_7$ and R$_8$ being the hydrogen atom or a C$_1$–C$_6$ alkyl radical;

a heterocyclic radical selected from the group consisting of pyridine and thiophene which is unsubstituted or substituted by one to four identical or different substituents selected from the group consisting of a halogen atom and a nitro, C$_1$–C$_6$ alkyl, C$_1$–C$_6$ O-alkyl and C$_1$–C$_6$ S-alkyl group;

or, when n is equal to 2, 3 or 4, a group —NR$_9$R$_{10}$, R$_9$ and R$_{10}$ simultaneously being a C$_1$–C$_6$ alkyl radical or forming, together with the nitrogen atom to which they are attached, a heterocycle selected from the group consisting of morpholine, piperidine and pyrrolidine;

R$_3$ and R$_4$ which are identical or different, are the hydrogen atom or a C$_1$–C$_6$ alkyl radical; and R$_5$ is a group —NHR$_{11}$, R$_{11}$ being a C$_1$–C$_6$ alkyl radical, a C$_3$–C$_7$-cycloalkyl radical, a C$_1$–C$_6$ alkyl chain possessing an alcohol or ether functional group, or a group —(CH)$_n$—NR$_9$R$_{10}$, n, R$_9$ and R$_{10}$ being as defined above, or a pharmaceutically acceptable addition salt thereof, in combination with a pharmaceutically acceptable excipient, vehicle or carrier.

13. A pharmaceutical composition with antihypertensive activity which comprises a pharmaceutically effective amount of at least one compound of formula (I):

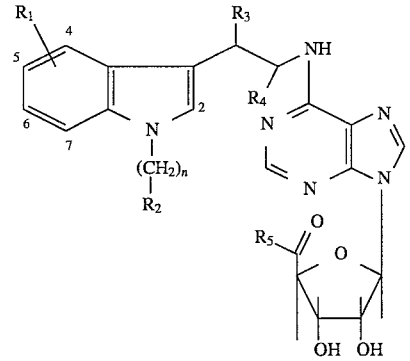

in which:

R$_1$ is a hydrogen atom, a halogen atom, a C$_1$–C$_6$ alkyl radical, a C$_1$–C$_6$ O-alkyl radical, a C$_1$–C$_6$ S-alkyl radical or a phenyl radical located in the 2-, 4-, 5-, 6- or 7-position of the indole;

n is an integer from 0 to 4;

R$_2$ is a C$_1$–C$_6$ alkyl radical, a C$_1$–C$_6$ alkenyl radical, C$_1$–C$_6$ alkynyl radical; a C$_3$–C$_7$-cycloalkyl radical or C$_1$–C$_6$ O-alkyl radical;

a phenyl or naphthyl radical which is unsubstituted or substituted by one to four identical or different substituents selected from the group consisting of a halogen atom, a nitro, C$_1$–C$_6$ alkyl, C$_1$–C$_6$ O-alkyl or C$_1$–C$_6$ S-alkyl group and a group —NR$_7$R$_8$, R$_7$ and R$_8$ being the hydrogen atom or a C$_1$–C$_6$ alkyl radical;

a heterocyclic radical selected from the group consisting of pyridine and thiophene which is unsubstituted or substituted by one to four identical or different substituents selected from the group consisting of a halogen atom and a nitro, C$_1$–C$_6$ alkyl, C$_1$–C$_6$ O-alkyl and C$_1$–C$_6$ S-alkyl group;

or, when n is equal to 2, 3 or 4, a group —NR$_9$R$_{10}$, R$_9$ and R$_{10}$ simultaneously being a C$_1$–C$_6$ alkyl radical or forming, together with the nitrogen atom to which they are attached, a heterocycle selected from the group consisting of morpholine, piperidine and pyrrolidine;

R$_3$ and R$_4$ which are identical or different, are the hydrogen atom or a C$_1$–C$_6$ alkyl radical; and R$_5$ is a group —NHR$_{11}$, R$_{11}$ being a C$_1$–C$_6$ alkyl radical, a C$_3$–C$_7$-cycloalkyl radical, a C$_1$–C$_6$ alkyl chain possessing an alcohol or ether functional group, or a group —(CH)$_n$—NR$_9$R$_{10}$, n, R$_9$ and R$_{10}$ being as defined above, or a pharmaceutically acceptable addition salt thereof, in combination with a pharmaceutically acceptable excipient, vehicle or carrier.

14. A method of preparing a pharmaceutical composition comprising incorporating at least one compound of formula (I):

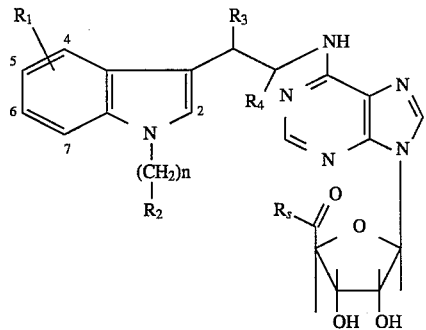

in which:

R$_1$ is a hydrogen atom, a halogen atom, a C$_1$–C$_6$ alkyl radical, a C$_1$–C$_6$ O-alkyl radical, a C$_1$–C$_6$ S-alkyl radical or a phenyl radical located in the 2-, 4-, 5-, 6- or 7-position of the indole;

n is an integer from 0 to 4;

R$_2$ is a C$_1$–C$_6$ alkyl radical, a C$_1$–C$_6$ alkenyl radical, C$_1$–C$_6$ alkynyl radical, a C$_3$–C$_7$-cycloalkyl radical or C$_1$–C$_6$ O-alkyl radical;

a phenyl or naphthyl radical which is unsubstituted or substituted by one to four identical or different substituents selected from the group consisting of a halogen atom, a nitro, C$_1$–C$_6$ alkyl, C$_1$–C$_6$ O-alkyl or C$_1$–C$_6$ S-alkyl group and a group —NR$_7$R$_8$, R$_7$ and R$_8$ being the hydrogen atom or a C$_1$–C$_6$ alkyl radical;

a heterocyclic radical selected from the group consisting of pyridine and thiophene which is unsubstituted or substituted by one to four identical or different substituents selected from the group consisting of a halogen atom and a nitro, C$_1$–C$_6$ alkyl, C$_1$–C$_6$ O-alkyl and C$_1$–C$_6$ S-alkyl group;

or, when n is equal to 2, 3 or 4, a group —NR$_9$R$_{10}$, R$_9$ and R$_{10}$ simultaneously being a C$_1$–C$_6$ alkyl radical or forming, together with the nitrogen atom to which they are attached, a heterocyclic selected from the group consisting of morpholine, piperidine and pyrroldine;

R$_3$ and R$_4$ which are identical or different, are the hydrogen atom or a C$_1$–C$_6$ alkyl radical; and R$_5$ is a group —NHR$_{11}$, R$_{11}$ being a C$_1$–C$_6$ alkyl radical, a C$_3$–C$_7$-cycloalkyl radical, a C$_1$–C$_6$ alkyl chain possessing an alcohol or ether functional group, or a group —(CH)$_n$—NR$_9$R$_{10}$, n, R$_9$ and R$_{10}$ being as defined above, or a pharmaceutically acceptable addition salt thereof, into a pharmaceutically acceptable excipient, vehicle or carrier.

15. A method according to claim 14 wherein the pharmaceutical composition is formulated as gelatin capsules or tablets containing from 5 to 300 mg of said compound of formula (I), or as injectable preparations containing from 0.1 to 100 mg of said compound of formula (I).

* * * * *

UNITED STATES PATENT AND TRADEMARK OFFICE
CERTIFICATE OF CORRECTION

PATENT NO. : 5,480,983
DATED : January 2, 1996
INVENTOR(S) : NICOLE BRU-MAGNIEZ et al It is certified that error appears in the above-indentified patent and that said Letters Patent is hereby corrected as shown below:

Title page:

after "[*] Notice:" change "April 5, 2011" to

-- The term of this patent shall not extend beyond the expiration date of Pat. No. 5,299,505 --

Signed and Sealed this

Eighth Day of April, 1997

Attest:

BRUCE LEHMAN

*Attesting Officer*    Commissioner of Patents and Trademarks